United States Patent
Cregg et al.

(10) Patent No.: US 8,222,386 B2
(45) Date of Patent: Jul. 17, 2012

(54) P. PASTORIS ADH PROMOTER AND USE THEREOF TO DIRECT EXPRESSION OF PROTEINS

(75) Inventors: James M. Cregg, Claremont, CA (US); Ilya I. Tolstorukov, Claremont, CA (US)

(73) Assignees: Keck Graduate Institute, Claremont, CA (US); Alder Biopharmaceuticals, Inc., Bothell, WA (US)

( * ) Notice: Subject to any disclaimer, the term of this patent is extended or adjusted under 35 U.S.C. 154(b) by 0 days.

(21) Appl. No.: 11/870,180

(22) Filed: Oct. 10, 2007

(65) Prior Publication Data

US 2008/0108108 A1 May 8, 2008

Related U.S. Application Data

(60) Provisional application No. 60/850,258, filed on Oct. 10, 2006.

(51) Int. Cl.
*C07H 21/04* (2006.01)
*C12N 15/11* (2006.01)
*C12N 15/63* (2006.01)
*C12N 1/19* (2006.01)

(52) U.S. Cl. ............... 536/24.1; 536/23.1; 435/320.1; 435/254.2

(58) Field of Classification Search ............... None
See application file for complete search history.

(56) References Cited

OTHER PUBLICATIONS

Cregg et al. Recent Advances in the Expression of Foreign Genes in *Pichia pastoris*. Biotechnology. Aug. 1993, vol. 11, pp. 905-910.

*Primary Examiner* — Michele K Joike
(74) *Attorney, Agent, or Firm* — Hunton & Williams LLP

(57) ABSTRACT

Novel promoters which are derived from *P. pastoris pastoris* which are inducible or repressible under specific growth conditions are provided. These promoters are useful for regulating the expression of a desired structural gene, e.g., a mammalian polypeptide. Particularly preferred is the use of these novel promoters to regulate gene expression in polyploidal yeast such as diploidal *P. pastoris* produced by mating or spheroplast fusion.

18 Claims, 4 Drawing Sheets

P. PASTORIS ADH PROMOTER AND USE THEREOF TO DIRECT EXPRESSION OF PROTEINS

This application claims priority to and incorporates by reference U.S. provisional Ser. No. 60/850,258 filed on Oct. 10, 2006. This provisional application is incorporated by reference in its entirety.

BACKGROUND OF THE INVENTION

Recombinant protein production is an essential activity for high throughput screening, functional validation, structural biology, and production of pharmaceutical polypeptides. *Escherichia coli* is a widely used organism for the expression of heterologous proteins because it easily grows to a high cell density on inexpensive substrates, and has well-established genetic techniques and expression vectors. However, this is not always sufficient for the efficient production of active biomolecules. In order to be biologically active, polypeptide chains have to fold into the correct native three-dimensional structure, including the appropriate formation of disulfide bonds, and may further require correct association of multiple chains.

Although the active state of the protein may be thermodynamically favored, the time-scale for folding can vary from milliseconds to days. Kinetic barriers are introduced, for example, by the need for alignment of subunits and sub-domains. And particularly with eukaryotic proteins, covalent reactions must take place for the correctly folded protein to form. The latter types of reaction include disulfide bond formation, cis/trans isomerization of the polypeptide chain around proline peptide bonds, preprotein processing and the ligation of prosthetic groups. These kinetic limitations can result in the accumulation of partially folded intermediates that contain exposed hydrophobic 'sticky' surfaces that promote self-association and formation of aggregates.

Recombinant synthesis of such complex proteins has had to rely on higher eukaryotic tissue culture-based systems for biologically active material. However, mammalian tissue culture based production systems are significantly more expensive and complicated than microbial fermentation methods. In addition, there continues to be questions regarding therapeutic products produced using materials derived from animal by-products.

As a eukaryote, *P. pastoris pastoris* has many of the advantages of higher eukaryotic expression systems such as protein processing, protein folding, and posttranslational modification, while being as easy to manipulate as *E. coli* or *Saccharomyces cerevisiae*. It is faster, easier, and less expensive to use than other eukaryotic expression systems such as baculovirus or mammalian tissue culture, and generally gives higher expression levels. As a yeast, it shares the advantages of molecular and genetic manipulations with *Saccharomyces*. These features make *P. pastoris* very useful as a protein expression system.

Many of the techniques developed for *Saccharomyces* may be applied to *P. pastoris*. These include transformation by complementation; gene disruption and gene replacement. In addition, the genetic nomenclature used for *Saccharomyces* has been applied to *P. pastoris*. There is also cross-complementation between gene products in both *Saccharomyces* and *P. pastoris*. Several wild-type genes from *Saccharomyces* complement comparable mutant genes in *P. pastoris*.

Heterologous expression in *P. pastoris pastoris* can be either intracellular or secreted. Secretion requires the presence of a signal sequence on the expressed protein to target it to the secretory pathway. While several different secretion signal sequences have been used successfully, including the native secretion signal present on some heterologous proteins, success has been variable. A potential advantage to secretion of heterologous proteins is that *P. pastoris pastoris* secretes very low levels of native proteins. That, combined with the very low amount of protein in the minimal *P. pastoris* growth medium, means that the secreted heterologous protein comprises the vast majority of the total protein in the medium and simple removal of the yeast cells serves as the first step in purification of the protein.

Many species of yeast, including *P. pastoris*, are mating competent. This enables two distinct haploid strains to mate naturally and generate a diploid species possessing two complete sets of chromosomal copies.

Although *P. pastoris* has been used successfully for the production of various heterologous proteins, e.g., hepatitis B surface antigen (Cregg et al. (1987) Bio/Technology 5:479), lysozyme and invertase (Digan et al. (1988) *Dev. Indust. Micro.* 29:59; Tschopp et al. (1987) *Bio/Technology* 5:1305), endeavors to produce other heterologous gene products in *P. pastoris*, especially by secretion, have given mixed results. At the present level of understanding of the *P. pastoris* expression system, it is unpredictable whether a given gene can be expressed to an appreciable level in this yeast or whether *P. pastoris* will tolerate the presence of the recombinant gene product in its cells. Further, it is especially difficult to foresee if a particular protein will be secreted by *P. pastoris*, and if it is, at what efficiency.

Various promoters have been derived from *P. pastoris pastoris* and used to regulate the expression of homologous and heterologous proteins in yeast. These promoters include in particular the alcohol oxidase promoters from the AOX1, AOX2 and mutant forms thereof as well as a promoter derived from the formaldehyde dehydrogenase gene FLD1. However, novel *P. pastoris* promoters especially *P. pastoris* promoters that are inducible or repressible under specific conditions and/or which provide for high expression yields in different yeast species are still needed.

The present invention satisfies this need and provides novel inducible promoters which are derived from *P. pastoris pastoris* and methods of use thereof to regulate the expression of structural genes operably linked thereto. In a preferred embodiment these promoters are used in the subject Assignee's proprietary improved methods and expression vectors that provide for the secretion of heterologous proteins, especially heteromultimers, from mating competent yeast, desirably polyploid yeast and most preferably diploid *P. pastoris* strains.

SUMMARY OF INVENTION

The invention provides novel inducible promoters derived from *P. pastoris* pastoris. In particular the invention provides the nucleic acid sequences for the ADH1, ENO1 and GUT1 genes of *P. pastoris pastoris*.

Also, the invention provides DNA constructs wherein these novel *P. pastoris pastoris* promoters or mutant, hybrid or chimeric promoters derived therefrom are operably linked to one or more structural genes, preferably structural genes encoding a multichain mammalian protein such as an immunoglobulin.

Also, the invention provides expression vectors, including autonomously replicating plasmids and vectors that integrate into a yeast's chromosomal DNA randomly or site specifically containing at least one novel yeast promoter according to the invention.

Further the invention provides transformed yeast, preferably transformed polyploidal strains containing said expression vectors.

Still further the invention provides methods of expressing proteins under specific regulated or inducible conditions by expressing a gene encoding said protein under the regulatory control of a novel promoter according to the invention under conditions that favor expression.

In addition, methods are provided for the synthesis and secretion of recombinant hetero-multimeric proteins in mating competent yeast wherein these hetero-multimeric proteins are expressed under the regulatory control of a novel *P. pastoris pastoris* promoter according to the invention. Hetero-multimeric proteins of special interest will comprise at least two non-identical polypeptide chains, e.g. antibody heavy and light chains, MHC alpha and beta chains; and the like. An expression vector is provided for each non-identical polypeptide chain wherein either or both contain a *P. pastoris* promoter according to the invention.

Each expression vector is transformed into a haploid yeast cell. In some embodiments of the invention, the haploid yeast cell is genetically marked, where the haploid yeast cell is one of a complementary pair. A first expression vector is transformed into one haploid cell and a second expression vector is transformed into a second haploid cell. Where the haploid cells are to be mated this will be through direct genetic fusion, or a similar event is induced with spheroplast fusion.

The expression levels of the non-identical polypeptides in the haploid cells may be individually calibrated, and adjusted through appropriate selection, vector copy number, promoter strength and/or induction and the like. In one embodiment of the invention, the promoter in each expression vector is different. In another embodiment of the invention, the same promoter is provided for each. The novel promoters provided herein are inducible, i.e., they are transcriptionally active or "on" only under specific carbon source conditions.

In this preferred embodiment, the transformed haploid cells, each individually synthesizing a non-identical polypeptide, are identified and then genetically crossed or fused. The resulting diploid strains are utilized to produce and secrete fully assembled and biologically functional hetero-multimeric protein. The diploid methodology allows optimized subunit pairing to enhance full-length product generation and secretion. However, the subject novel promoters may alternatively be used in conventional (non-polyploidal) yeast expression methods as well.

BRIEF DESCRIPTION OF THE DRAWINGS

FIG. 1B shows selective detection of the H chain, which is found only in the parental H chain haploid, and mated diploid containing both H and L. FIG. 1C shows general detection of H and L chains, which establishes that protein production is active in all three strains. FIG. 1D shows selective detection in the diploid strain of correctly assembled full antibody, confirming that only the diploid system is capable of generating fully assembled antibody.

DETAILED DESCRIPTION OF THE EMBODIMENTS

Figure 1:
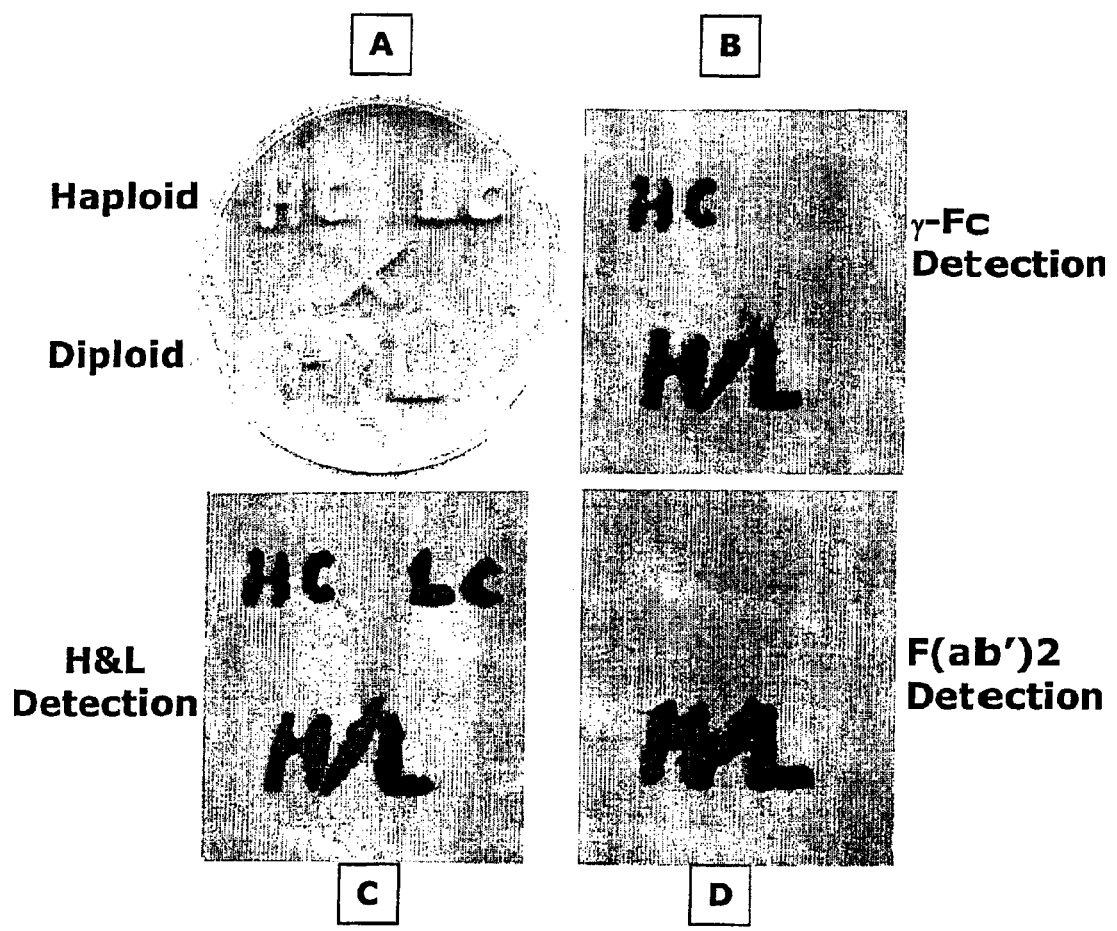
FIGS. 1A-1D. Generation of assembled full length recombinant antibody. Immunoblot detection methodology was used to characterize the parental haploid *P. pastoris* strains, each producing a subunit of the antibody and target diploid strain producing both subunits that form the fully assembled antibody. The yeast strains shown in FIG. 1A show a static culture of each of the representative strains, where the top portion is the distinct haploids strains containing Heavy (H) and Light (L) chain subunits respectively; the bottom the mated stable diploid producing both subunits.

The present Assignee, Alder Biopharmaeuticals Inc., has developed methods for using polyploidal *P. pastoris* and other yeast species into a robust scalable platform for industrial scale production of heterologous proteins for commercial applications. These methods are generically applicable for expressing any desired protein. However, in preferred embodiments this expression system is utilized to produce mammalian proteins, especially mammalian polypeptides such as multichain proteins having therapeutic or diagnostic applications, such as antibodies, enzymes, hormones, growth factors, cytokines, and the like. It has been surprisingly discovered that polyploidal yeast express heterologous proteins, including multichain proteins such as immunoglobulins for prolonged time periods and at very high yields.

While these methods are described and exemplified in the Assignee's earlier patent applications, it is desired to further enhance these methods. Along these lines it is a continuing objective of the Assignee to identify regulatory sequences and specific mutants or culture methods that provide for even higher protein yields or which are desirable from other perspectives such as enhanced stability. There is a specific need to expand the repertoire of promoters available for use in *P. pastoris* that provide for inducible gene expression. Current inducible promoter systems employ materials that pose significant hazards at the scale-up stage. The present invention as described in detail herein provides a series of novel inducible promoters that employ inexpensive, non-hazardous induction alternatives to the currently available *P. pastoris* promoter induction systems. Particularly, the present invention identifies three novel regulatory sequences derived from *P. pastoris* genes, i.e., ADH1 or alcohol dehydrogenase 1, glycerol kinase (GUT1) and enolase (ENO1). The sequences for these three novel promoters are provided infra.

These novel promoters are desirably used to effect the expression of recombinant hetero-multimeric proteins, which are preferably secreted from diploid strains of mating competent yeast. In this preferred embodiment of the invention a pair of genetically marked yeast haploid cells are transformed with expression vectors comprising subunits of the hetero-multimeric protein operably linked to a novel promoter according to the invention. One haploid cell comprises a first expression vector, and a second haploid cell comprises a second expression vector wherein either or both may contain a novel promoter according to the invention. Optionally, additional expression vectors may be introduced into the haploid or diploid cells; or the first or second expression vectors may comprise additional coding sequences; for the synthesis of heterotrimers; heterotetramers; etc. The expression levels of the non-identical polypeptides may be individually calibrated, and adjusted through appropriate selection, vector copy number, promoter strength and/or induction and the like. The transformed haploid cells are genetically crossed or fused. The resulting diploid or tetraploid strains are utilized to produce and secrete fully assembled and biologically functional hetero-multimeric protein under the regulatory control of at least one promoter according to the invention.

As disclosed in the Assignee's earlier patent applications, the use of diploid or tetraploid cells for protein production provides for unexpected benefits. The cells can be grown for production purposes, i.e. scaled up, and for extended periods of time, in conditions that can be deleterious to the growth of haploid cells, which conditions may include high cell density; growth in minimal medium; growth at low temperatures; stable growth in the absence of selective pressure; and which may provide for maintenance of heterologous gene sequence integrity and maintenance of high level expression over time. These benefits may arise, at least in part, from the creation of diploid strains from two distinct parental haploid strains. Such haploid strains can comprise numerous minor autotrophic mutations, which mutations are complemented in the diploid or tetraploid, enabling growth under highly selective conditions.

DEFINITIONS

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

Mating competent yeast species. Such species of yeast exist in a haploid and a diploid form. The diploid cells may, under appropriate conditions, proliferate for indefinite number of generations in the diploid form. Diploid cells can also sporulate to form haploid cells. In addition, sequential mating can result in tetraploid strains through further mating of the auxotrophic diploids.

In one embodiment of the invention, the mating competent yeast is a member of the Saccharomycetaceae family, which includes the genera *Arxiozyma; Ascobotryozyma; Citeromyces; Debaryomyces; Dekkera; Eremothecium; Issatchenkia; Kazachstania; Kluyveromyces; Kodamaea; Lodderomyces; Pachysolen; P. pastoris; Saccharomyces; Saturnispora; Tetrapisispora; Torulaspora; Williopsis*; and *Zygosaccharomyces*.

The genus *P. pastoris* is of particular interest. *P. pastoris* comprises a number of species, including the species *P. pastors pastoris, P. pastoris methanolica*, and *Hansenula polymorpha* (*P. pastoris angusta*). Most preferred is the species *P. pastoris*.

Haploid Yeast Cell: A cell having a single copy of each gene of its normal genomic (chromosomal) complement.

Diploid Yeast Cell: A cell having two copies (alleles) of every gene of its normal genomic complement, typically formed by the process of fusion (mating) of two haploid cells.

Tetraploid Yeast Cell. A cell having four copies (alleles) of every gene of its normal genomic complement, typically formed by the process of fusion (mating) of two haploid cells. Tetraploids may carry two, three, or four different cassettes. Such tetraploids might be obtained in *S. cerevisiae* by selective mating of homozygotic heterothallic a/a and alpha/alpha diploids and in *P. pastoris* by sequential mating of haploids to obtain auxotrophic diploids. For example, a [met his] haploid can be mated with [ade his] haploid to obtain diploid [his]; and a [met arg] haploid can be mated with [ade arg] haploid to obtain diploid [arg]; then the diploid [his] x diploid [arg] to obtain a tetraploid prototroph. It will be understood by those of skill in the art that reference to the benefits and uses of diploid cells may also apply to tetraploid cells.

Yeast Mating: The process by which two haploid yeast cells naturally fuse to form one diploid yeast cell.

Meiosis: The process by which a diploid yeast cell undergoes reductive division to form four haploid spore products. Each spore may then germinate and form a haploid vegetatively growing cell line.

Selectable Marker: A selectable marker is a gene or gene fragment that confers a growth phenotype (physical growth characteristic) on a cell receiving that gene as, for example through a transformation event. The selectable marker allows that cell to survive and grow in a selective growth medium under conditions in which cells that do not receive that selectable marker gene cannot grow. Selectable marker genes generally fall into several types, including positive selectable marker genes such as a gene that confers on a cell resistance to an antibiotic or other drug, temperature-sensitive (ts) mutants, including both cold-sensitive and heat-sensitive mutants, e.g., when two ts mutants are crossed or a ts mutant is transformed; negative selectable marker genes such as a biosynthetic gene that confers on a cell the ability to grow in a medium without a specific nutrient needed by all cells that do not have that biosynthetic gene, or a mutagenized biosynthetic gene that confers on a cell inability to grow by cells that do not have the wild type gene; and the like. Suitable markers and ts mutants are well known and readily available and include but are not limited to: ZEO; G418; HIS 5; LYS3; MET1; MET3a; ADEL; ADE3; URA3; and the like.

Expression Vector: These DNA species contain elements that facilitate manipulation for the expression of a foreign protein within the target host cell. Conveniently, manipulation of sequences and production of DNA for transformation is first performed in a bacterial host, e.g. *E. coli* and usually vectors will include sequences to facilitate such manipulations, including a bacterial origin of replication and appropriate bacterial selection marker. Selectable markers encode proteins necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, (b) complement auxotrophic deficiencies, or (c) supply critical nutrients not available from complex media.

Expression vectors for use in the methods of the invention will further include yeast specific sequences, including a selectable auxotrophic or drug marker for identifying transformed yeast strains. A drug marker may further be used to amplify copy number of the vector in a yeast host cell.

The polypeptide coding sequence of interest is operably linked to transcriptional and translational regulatory sequences that provide for expression of the polypeptide in yeast cells. These vector components may include, but are not limited to, one or more of the following: an enhancer element, a promoter, and a transcription termination sequence. Sequences for the secretion of the polypeptide may also be included, e.g. a signal sequence, and the like. A yeast origin of replication is optional, as expression vectors are often integrated into the yeast genome.

In one embodiment of the invention, the polypeptide of interest is operably linked, or fused, to sequences providing for optimized secretion of the polypeptide from yeast diploid cells.

Nucleic acids are "operably linked" when placed into a functional relationship with another nucleic acid sequence. For example, DNA for a signal sequence is operably linked to DNA for a polypeptide if it is expressed as a preprotein that participates in the secretion of the polypeptide; a promoter or enhancer is operably linked to a coding sequence if it affects the transcription of the sequence. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites or alternatively via a PCR/recombination method familiar to those skilled in the art (Gateway® Technology; Invitrogen, Carlsbad Calif.). If such sites do not exist, the synthetic oligonucleotide adapters or linkers are used in accordance with conventional practice.

Promoters are untranslated sequences located upstream (5') to the start codon of a structural gene (generally within about 100 to 1000 bp) that control the transcription and translation of particular nucleic acid sequence to which they are operably linked. Such promoters fall into several classes: inducible, constitutive, and repressible promoters that increase levels of transcription in response to absence of a repressor. Inducible promoters may initiate increased levels of transcription from DNA under their control in response to some change in culture conditions, e.g., the presence or absence of a nutrient or a change in temperature.

The yeast promoter fragment may also serve as the site for homologous recombination and integration of the expression vector into the same site in the yeast genome; alternatively a selectable marker is used as the site for homologous recombination. P. pastoris transformation is described in Cregg et al. (1985) Mol. Cell. Biol. 5:3376-3385.

Examples of previously known promoters from P. pastoris useful for heterologous gene expression include the AOX1 promoter (Cregg et al. (1989) Mol. Cell. Biol. 9:1316-1323); ICL1 promoter (Menendez et al. (2003) Yeast 20(13):1097-108); glyceraldehyde-3-phosphate dehydrogenase promoter (GAP) (Waterham et al. (1997) Gene 186(1):37-44); and FLD1 promoter (Shen et al. (1998) Gene 216(1):93-102). The GAP promoter is a strong constitutive promoter and the AOX and FLD1 promoters are inducible.

As previously noted this invention provides three novel promoter sequences derived from the ADH1, ENO1 and GUT1 genes of P. pastoris. It should be understood that these promoters may comprise the specific nucleic acid sequences provided herein, as well as fragments, mutants and chimeric prompters derived using these novel promoter sequences. For example, the subject promoter sequences may be truncated and the fragments screened to assess those truncated sequences still provide for transcription of a gene operably linked thereto. Alternatively different 5' portions of the promoter regions described herein may be directly or indirectly linked to other promoters, especially strong constitutive promoters in order to obtain a chimeric or hybrid promoter that is rendered inducible under the conditions that the ADH1, ENO1 or GUT1 promoter is inducible. Still alternatively the subject promoters may be mutagenized by site specific mutagenesis at one or more sites, e.g., from 1-50 residues, 1-25 residues, 1-10 residues or 1-5 residues and the mutant promoter sequences screened to determine the effect of such mutations on the levels of expression or induction on structural genes operably linked thereto For example, these methods may be used to identify mutant promoters which are stronger relative to the wild-type ADH1, ENO1 or GUT1 promoters, or which are "tighter or less leaky", i.e. do not turn on unless the induction conditions are present. This may be advantageous in the situation wherein the expressed heterologous protein is toxic to the yeast cell it is being expressed in. Also the invention provides promoters that hybridize to the subject novel promoters under stringent hybridization conditions.

The polypeptides of interest which are operably linked to a promoter according to the invention may be produced recombinantly not only directly, but also as a fusion polypeptide with a heterologous polypeptide, e.g. a signal sequence or other polypeptide having a specific cleavage site at the N-terminus of the mature protein or polypeptide. In general, the signal sequence may be a component of the vector, or it may be a part of the polypeptide coding sequence that is inserted into the vector. The heterologous signal sequence selected preferably is one that is recognized and processed through one of the standard pathways available within the host cell. The S. cerevisiae alpha factor pre-pro signal has proven effective in the secretion of a variety of recombinant proteins from P. pastoris. Secretion signals of interest also include mammalian signal sequences, which may be heterologous to the protein being secreted, or may be a native sequence for the protein being secreted. Signal sequences include pre-peptide sequences, and in some instances may include propeptide sequences. Many such signal sequences are known in the art, including the signal sequences found on immunoglobulin chains, e.g. kappa 28 preprotoxin sequence, PHA-E, FACE, human MCP-1, human serum albumin signal sequences, human Ig heavy chain, human Ig κ light chain, and the like. For example, see Hashimoto et. al. Protein Eng 11(2) 75 (1998); and Kobayashi et. al. Therapeutic Apheresis 2(4) 257 (1998).

Transcription may be further increased by inserting a transcriptional activator sequence into the promoter containing vector. These activators are cis-acting elements of DNA, usually about from 10 to 300 bp, which act on a promoter to increase its transcription. Transcriptional enhancers are relatively orientation and position independent, having been found 5' and 3' to the transcription unit, within an intron, as well as within the coding sequence itself. The enhancer may be spliced into the expression vector at a position 5' or 3' to the coding sequence, but is preferably located at a site 5' from the promoter.

Expression vectors used in eukaryotic host cells may also contain sequences necessary for the termination of transcription and for stabilizing the mRNA. Such sequences are commonly available from 3' to the translation termination codon, in untranslated regions of eukaryotic or viral DNAs or cDNAs. These regions contain nucleotide segments transcribed as polyadenylated fragments in the untranslated portion of the mRNA.

Construction of suitable vectors containing one or more of the above-listed components employs standard ligation techniques or PCR/recombination methods. Isolated plasmids or DNA fragments are cleaved, tailored, and re-ligated in the form desired to generate the plasmids required via recombination methods. For analysis to confirm correct sequences in plasmids constructed, the ligation mixtures are used to transform host cells, and successful transformants selected by antibiotic resistance (e.g. ampicillin or Zeocin) where appropriate. Plasmids from the transformants are prepared, analyzed by restriction endonuclease digestion and/or sequenced.

As an alternative to restriction and ligation of fragments, site specific recombination methods based on, for example att sites and recombination enzymes may be used to insert DNA sequences into a vector. Such methods are described, for example, by Landy (1989) Ann. Rev. Biochem. 58:913-949; and are known to those of skill in the art. Such methods utilize intermolecular DNA recombination that is mediated by a lambda phage and *E. coli*-encoded recombination proteins. Recombination occurs between specific attachment (att) sites on the interacting DNA molecules. For a description of att sites see Weisberg and Landy (1983) Site-Specific Recombination in Phage Lambda, in *Lambda II*, Weisberg, ed. (Cold Spring Harbor, N.Y.: Cold Spring Harbor Press), pp. 211-250. The DNA segments flanking the recombination sites are switched, such that after recombination, the att sites are hybrid sequences comprised of sequences donated by each parental vector. The recombination can occur between DNAs of any topology.

att sites may be introduced into a sequence of interest by ligating the sequence of interest into an appropriate vector; generating a PCR product containing att B sites through the use of specific primers; generating a cDNA library cloned into an appropriate vector containing att sites; and the like.

Folding, as used herein, refers to the three-dimensional structure of polypeptides and proteins, where interactions between amino acid residues act to stabilize the structure. While non-covalent interactions are important in determining structure, usually the proteins of interest will have intra- and/or intermolecular covalent disulfide bonds formed by two cysteine residues. For naturally occurring proteins and polypeptides or derivatives and variants thereof, the proper folding is typically the arrangement that results in optimal biological activity, and can conveniently be monitored by assays for activity, e.g. ligand binding, enzymatic activity, etc.

In some instances, for example where the desired product is of synthetic origin, assays based on biological activity will be less meaningful. The proper folding of such molecules may be determined on the basis of physical properties, energetic considerations, modeling studies, and the like.

The expression host may be further modified by the introduction of sequences encoding one or more enzymes that enhance folding and disulfide bond formation, i.e. foldases, chaperonins, etc. Such sequences may be constitutively or inducibly expressed in the yeast host cell, using vectors, markers, etc. as known in the art. Preferably the sequences, including transcriptional regulatory elements sufficient for the desired pattern of expression, are stably integrated in the yeast genome through a targeted methodology.

For example, the eukaryotic PDI is not only an efficient catalyst of protein cysteine oxidation and disulfide bond isomerization, but also exhibits chaperone activity. Co-expression of PDI can facilitate the production of active proteins having multiple disulfide bonds. Also of interest is the expression of BIP (immunoglobulin heavy chain binding protein); cyclophilin; and the like. In one embodiment of the invention, each of the haploid parental strains expresses a distinct folding enzyme, e.g. one strain may express BIP, and the other strain may express PDI.

The terms "desired protein" or "target protein" are used interchangeably and refer generally to any secreted protein having 2 or more non-identical polypeptide chains, where such chains are independently synthesized, i.e. not resulting from post-translational cleavage of a single polypeptide chain. The polypeptides are heterologous, i.e., foreign, to the yeast. Preferably, mammalian polypeptides, i.e. polypeptides encoded in a mammalian genome are used.

In a preferred embodiment, the protein is an antibody. The term "antibody" is intended to include any polypeptide chain-containing molecular structure with a specific shape that fits to and recognizes an epitope, where one or more non-covalent binding interactions stabilize the complex between the molecular structure and the epitope. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammals, chicken, other avians, etc., are considered to be "antibodies." Numerous antibody coding sequences have been described; and others may be raised by methods well-known in the art.

For example, antibodies or antigen binding fragments may be produced by genetic engineering. In this technique, as with other methods, antibody-producing cells are sensitized to the desired antigen or immunogen. The messenger RNA isolated from antibody producing cells is used as a template to make cDNA using RT-PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host cell. When antibody gene synthesis is induced in the transfected host, the heavy and light chain proteins self-assemble to produce active antibodies that can be detected by screening with the antigen or immunogen.

Antibody coding sequences of interest include those encoded by native sequences, as well as nucleic acids that, by virtue of the degeneracy of the genetic code, are not identical in sequence to the disclosed nucleic acids, and variants thereof. Variant polypeptides can include amino acid (aa) substitutions, additions or deletions. The amino acid substitutions can be conservative amino acid substitutions or substitutions to eliminate non-essential amino acids, such as to alter a glycosylation site, or to minimize misfolding by substitution or deletion of one or more cysteine residues that are not necessary for function. Variants can be designed so as to retain or have enhanced biological activity of a particular region of the protein (e.g., a functional domain, catalytic amino acid residues, etc). Variants also include fragments of the polypeptides disclosed herein, particularly biologically active fragments and/or fragments corresponding to functional domains. Techniques for in vitro mutagenesis of cloned genes are known. Also included in the subject invention are polypeptides that have been modified using ordinary molecular biological techniques so as to improve their resistance to proteolytic degradation or to optimize solubility properties or to render them more suitable as a therapeutic agent.

Chimeric antibodies may be made by recombinant means by combining the variable light and heavy chain regions (VK and VH), obtained from antibody producing cells of one species with the constant light and heavy chain regions from another. Typically chimeric antibodies utilize rodent or rabbit variable regions and human constant regions, in order to produce an antibody with predominantly human domains. The production of such chimeric antibodies is well known in the art, and may be achieved by standard means (as described, e.g., in U.S. Pat. No. 5,624,659, incorporated fully herein by reference).

Humanized antibodies are engineered to contain even more human-like immunoglobulin domains, and incorporate only the complementarity-determining regions of the animal-derived antibody and in certain instances a subset of this foreign CDR sequences. This is accomplished by carefully examining the sequence of the hyper-variable loops of the variable regions of the monoclonal antibody, and fitting them to the structure of the human antibody chains. Although facially complex, the process is straightforward in practice. See, e.g., U.S. Pat. No. 6,187,287, incorporated fully herein by reference.

In addition to entire immunoglobulins (or their recombinant counterparts), immunoglobulin fragments comprising the epitope binding site (e.g., Fab', F(ab')$_2$, or other fragments) may be synthesized. "Fragment," or minimal immunoglobulins may be designed utilizing recombinant immunoglobulin techniques. For instance "Fv" immunoglobulins for use in the present invention may be produced by synthesizing a variable light chain region and a variable heavy chain region. Combinations of antibodies are also of interest, e.g. diabodies, which comprise two distinct Fv specificities.

Immunoglobulins may be modified post-translationally, e.g. to add chemical linkers, detectable moieties, such as fluorescent dyes, enzymes, substrates, chemiluminescent moieties and the like, or specific binding moieties, such as streptavidin, avidin, or biotin, and the like may be utilized in the methods and compositions of the present invention.

Preferred Methods of Polypeptide Synthesis According to the Invention

As noted above, the subject novel *P. pastoris* promoters may be used in any compatible eukaryotic expression system but preferably are used in the Assignee's proprietary polyploid expression system This system can be used to produce single or multiple subunit polypeptides. If used to produce a multiple subunit polypeptide such as an immunoglobulin the expression system may be carried out as follows:

Transformed mating competent haploid yeast cells provide a genetic method that enables subunit pairing of a desired protein. Haploid yeast strains, preferably two differently marked haploids strains, are transformed with each of two expression vectors, a first vector to direct the synthesis of one polypeptide chain and a second vector to direct the synthesis of a second, non-identical polypeptide chain. The two haploid strains are mated to provide a diploid host where optimized target protein production can be obtained. However, alternatively and less preferably a single haploid strain may be transformed with two vectors or a single vector that provides for the expression of both polypeptide subunits and the resultant transformed haploid mated or fused with another haploid to produce a diploid that expresses the multiple subunit polypeptide.

Optionally, additional non-identical coding sequence(s) are provided. Such sequences may be present on additional expression vectors or in the first or the second expression vectors. As is known in the art, multiple coding sequences may be independently expressed from individual promoters; or may be coordinately expressed through the inclusion of an "internal ribosome entry site" or "IRES", which is an element that promotes direct internal ribosome entry to the initiation codon, such as ATG, of a cistron (a protein encoding region), thereby leading to the cap-independent translation of the gene. IRES elements functional in yeast are described by Thompson et al. (2001) *P.N.A.S.* 98:12866-12868.

In one embodiment of the invention, antibody sequences are produced in combination with a secretory J chain, which provides for enhanced stability of IgA (see U.S. Pat. Nos. 5,959,177; and 5,202,422).

The two haploid yeast strains are each auxotrophic, and require supplementation of media for growth of the haploid cells. The pair of auxotrophs are complementary, such that the diploid product will grow in the absence of the supplements required for the haploid cells. Many such genetic markers are known in yeast, including requirements for amino acids (e.g. methionine, lysine, histidine, arginine, etc.), nucleosides (e.g. uracil, adenine, etc.); and the like. Amino acid markers may be preferred for the methods of the invention.

The two transformed haploid cells may be genetically crossed and diploid strains arising from this mating event selected by their hybrid nutritional requirements. Alternatively, populations of the two transformed haploid strains are spheroplasted and fused, and diploid progeny regenerated and selected. By either method, diploid strains can be identified and selectively grown because, unlike their haploid parents, they do not have the same nutritional requirements. For example, the diploid cells may be grown in minimal medium. The diploid synthesis strategy has certain advantages. Diploid strains have the potential to produce enhanced levels of heterologous protein through broader complementation to underlying mutations, which may impact the production and/or secretion of recombinant protein.

In one embodiment of the invention, each of the haploid strains is transformed with a library of polypeptides, e.g. a library of antibody heavy or light chains. Transformed haploid cells that synthesize the polypeptides are mated with the complementary haploid cells and may display the protein on their cell surface. This methodology which essentially comprises the construction and diversification of yeast cell surface displayed libraries produced by mating has been extensively used in particular for affinity maturation of Fab antibody fragments. (See e.g., Blaise L et. al. Gene (2004) 342:211-8; and patents assigned to Cambridge Antibody Technology such as U.S. Pat. Nos. 7,063,943; 6,916,605; 6,806,079; 6,172,197; 5,969,108; and 5,565,332, all of which are incorporated by reference in their entireties herein). The resulting diploid cells are screened for functional protein. The diploid cells provide a means of rapidly, conveniently and inexpensively bringing together a large number of combinations of polypeptides for functional testing. This technology is especially applicable for the generation of heterodimeric protein products, where optimized subunit synthesis levels are critical for functional protein expression and secretion. As noted yeast display is well used for affinity maturation of Fab fragments. In addition it has recently been shown that Fab antibodies can be displayed on the cell surface of *Saccharomyces cerevisiae* and that affinity matured Fab antibody fragments sorted by fluorescent-activated cell sorting of yeast-displayed libraries have been identified. (See, Van den Buecken et al., FEBS Letters 546:288-294 (2003)) This discovery and the knowledge that Fab antibodies are heterodimeric suggests that independent repertoires of heavy chain (HC) and light chain (LC) can be constructed in haploid yeast strains of opposite mating type. These separate repertoires can then be combined by highly efficient yeast mating. Using this approach, the present inventors have rapidly generated a naïve human Fab yeast display library of over a billion clones. In addition, utilizing error-prone polymerase chain reaction, the inventors have diversified Fab sequences and generated combinatorial and hierarchal chain shuffled libraries with complexities of up to 5 billion clones. These libraries can be selected for higher affinity using a repetitive process of mating-driven chain shuffling and flow cytometric sorting.

In another embodiment of the invention, the expression level ratio of the two subunits is regulated in order to maximize product generation. Heterodimer subunit protein levels have been shown previously to impact the final product generation (Simmons L C, J Immunol Methods. 2002 May 1; 263(1-2):133-47). Regulation can be achieved prior to the mating step by selection for a marker present on the expression vector. By stably increasing the copy number of the vector, the expression level can be increased. In some cases, it may be desirable to increase the level of one chain relative to the other, so as to reach a balanced proportion between the subunits of the polypeptide. Antibiotic resistance markers are useful for this purpose, e.g. Zeocin resistance marker, G418 resistance, etc. and provide a means of enrichment for strains that contain multiple integrated copies of an expression vector in a strain by selecting for transformants that are resistant to higher levels of Zeocin or G418. The proper ratio, e.g. 1:1; 1:2; etc. of the subunit genes may be important for efficient protein production. Even when the same promoter is used to transcribe both subunits, many other factors contribute to the final level of protein expressed and therefore, it can be useful to increase the number of copies of one encoded gene relative to the other. Alternatively, diploid strains that produce higher levels of a polypeptide, relative to single copy vector strains, are created by mating two haploid strains, both of which have multiple copies of the expression vectors.

Host cells are transformed with the above-described expression vectors, mated to form diploid strains, and cultured in conventional nutrient media modified as appropriate for the subject novel inducible promoters, selecting transformants or amplifying the genes encoding the desired sequences. As described infra in the examples the subject novel inducible promoters are strongly inducible in the presence of at least one of glycerol and ethanol and/or repressed by methanol. The induction medium will therefore contain these carbon sources or another carbon source that similarly induces the promoter. With respect thereto a number of minimal media suitable for the growth of yeast are known in the art. Any of these media may be supplemented as necessary with salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression, and will be apparent to the ordinarily skilled artisan.

Secreted proteins are recovered from the culture medium. A protease inhibitor, such as phenyl methyl sulfonyl fluoride (PMSF) may be useful to inhibit proteolytic degradation during purification, and antibiotics may be included to prevent the growth of adventitious contaminants. The composition may be concentrated, filtered, dialyzed, etc., using methods known in the art.

The diploid cells of the invention are grown for production purposes. Such production purposes desirably include growth in minimal media, which media lacks pre-formed amino acids and other complex biomolecules, e.g. media comprising ammonia as a nitrogen source, and glucose as an energy and carbon source, and salts as a source of phosphate, calcium and the like. Preferably such production media lacks selective agents such as antibiotics, purines, pyrimidines, etc. The diploid cells can be grown to high cell density, for example at least about 50 g/L; more usually at least about 100 g/L; and may be at least about 300, about 400, about 500 g/L or more. If the heterologous protein is potentially adverse to yeast growth it may be desirable to initially grow the cells to high density under non-induction conditions, i.e., the absence of glycerol or ethanol and thereafter culture the expanded yeast cells under induction growth conditions.

In one embodiment of the invention, the growth of the subject cells for production purposes is performed at low temperatures, which temperatures may be lowered during log phase, during stationary phase, or both. The term "low temperature" refers to temperatures of at least about 15° C., more usually at least about 17° C., and may be about 20° C., and is usually not more than about 25-30° C., more usually not more than about 26° C. Growth temperature can impact the production of full-length secreted proteins in production cultures, and decreasing the culture growth temperature can strongly enhances the intact product yield. The decreased temperature appears to assist intracellular trafficking through the folding and post-translational processing pathways used by the host to generate the target product, along with reduction of cellular protease degradation.

The methods of the invention provide for expression of secreted, active protein, particularly secreted, active antibodies, where "active antibodies", as used herein, refers to a correctly folded multimer of at least two properly paired chains, which accurately binds to its cognate antigen. Expression levels of active protein are usually at least about 50 mg/liter culture, more usually at least about 100 mg/liter, preferably at least about 500 mg/liter, and may be 1000 mg/liter or more.

The methods of the invention can provide for increased stability of the host and heterologous coding sequences during production. The stability is evidenced, for example, by maintenance of high levels of expression over time, where the starting level of expression is decreased by not more than about 20%, usually not more than 10%, and may be decreased by not more than about 5% over about 20 doublings, 50 doublings, 100 doublings, or more.

The strain stability is believed to also provide for maintenance of heterologous gene sequence integrity over time, where the sequence of the active coding sequence and requisite transcriptional regulatory elements are maintained in at least about 99% of the diploid cells, usually in at least about 99.9% of the diploid cells, and preferably in at least about 99.99% of the diploid cells over about 20 doublings, 50 doublings, 100 doublings, or more. Preferably, substantially all of the diploid cells will maintain the sequence of the active coding sequence and requisite transcriptional regulatory elements.

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention, which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

Example 1

To demonstrate the efficacy of the diploid expression method of the present invention for expressing an antibody the following reagents were prepared. It should be understood that these methods may be varied by the substitution of the conventional yeast promoters used therein (e.g. from the GAP and AOX1) with at least one of the novel inducible *P. pastoris pastoris* promoters from the ADH1, ENO1 and GUT1 genes disclosed in the Example which follows. This Example is intended therefore to be illustrative of the preferred diploid expression system and not of the efficacy of these novel promoters.

Antibody genes: Genes were cloned and constructed that directed the synthesis of three forms of a chimeric humanized mouse monoclonal antibody OKT3. The sources of the variable regions for use in these constructs can be found in Genbank. Accession number A22261; mouse OKT3 heavy chain (International Patent Application WO 9109967-A 3 11 Jul. 1991). Accession number A22259; mouse OKT3 light chain (International Patent Application WO 9109967-A 3 11 Jul. 1991).

All three forms utilized the identical $V_\kappa C_\kappa$, light chain gene (SEQ ID NO: 10). For the three heavy chain genes, all encoded the identical mouse variable region ($V_h$) but differed from each other in the amino acid sequence of the human heavy chain constant regions. The first construct directed the synthesis of a full-length wild-type heavy chain ($C_{\gamma 1}$) with its single normal N-linked glycosylation site present (full-length glycosylated heavy chain) (SEQ ID NO: 13 and No 14). The second gene directed the synthesis of a non-glycosylated heavy chain created by mutating a nucleotide in the sequence so that a threonine at position 301 was changed to an alanine in the glycosylation site recognition sequence (Asn-X-Thr/Ser) (full-length non-glycosylated heavy chain) (SEQ ID NO: 15). The third gene construct directed the synthesis of a heavy chain in which most of the constant region was deleted after the hinge region (Fab heavy chain) (SEQ ID NO: 16).

Expression vector: The vector contains the following functional components: 1) a mutant ColE1 origin of replication, which facilitates the replication of the plasmid vector in cells of the bacterium *Escherichia coli;* 2) a bacterial Sh ble gene, which confers resistance to the antibiotic Zeocin and serves as the selectable marker for transformations of both *E. coli* and *P. pastoris;* 3) an expression cassette composed of the glyceraldehyde dehydrogenase gene (GAP gene) promoter, fused to sequences encoding the *Saccharomyces cerevisiae* alpha mating factor pre pro secretion leader sequence, followed by sequences encoding a *P. pastoris* transcriptional termination signal from the *P. pastoris* alcohol oxidase I gene (AOX1). The Zeocin resistance marker gene provides a means of enrichment for strains that contain multiple integrated copies of an expression vector in a strain by selecting for transformants that are resistant to higher levels of Zeocin.

*P. pastoris* strains: The auxotrophic strains used for this example are the *P. pastoris* ade1 and ura3 strains, which require supplementation with adenine and uracil, respectively, for growth. Strains met1 and lys3 have also been used. Although any two complementing sets of auxotrophic strains could be used for the construction and maintenance of diploid strains, these two strains are especially suited for this method for two reasons. First, they grow more slowly than diploid strains that are the result of their mating or fusion. Thus, if a small number of haploid ade1 or ura3 cells remain present in a culture or arise through meiosis or other mechanism, the diploid strain should outgrow them in culture. The preferred strains for use in the subject *P. pastoris* diploid expression system are met1 and lys3.

The second is that it is easy to monitor the sexual state of these strains since colonies of the diploid product of their mating are a normal white or cream color, whereas cells of any strains that are haploid ade1 mutants in a culture form a colony with distinct pink in color. In addition, any strains that are haploid ura3 mutants are resistant to the drug 5-fluoro-orotic acid (FOA) and can be sensitively identified by plating samples of a culture on minimal medium+uracil plates with FOA. On these plates, only uracil-requiring ura3 mutant (presumably haploid) strains can grow and form colonies. Thus, with haploid parent strains marked with ade1 and ura3, one can readily monitor the sexual state of the resulting antibody-producing diploid strains (haploid versus diploid).

Methods

Construction of pGAPZ-alpha expression vectors for transcription of light and heavy chain antibody genes. For cloning of both the light and heavy chain variable regions, cells of a mouse OKT3 CD3 hybridoma cell line were grown and total RNA extracted. Two RT-PCR reactions were then performed, one specific to light and one specific to heavy chain variable region encoding sequences of the OKT3 antibody genes. The primers employed to amplify out the heavy and light chain variable region were (SEQ ID NO:1) 5'-CCGCTCGAGAAAAGAGAGGCTGAAGCTCAGGTCCAGCTGCAGCAGTC-3' and (SEQ ID NO:3) 5'-CCGCTCGAGAAGAGAGGCTGAAGCTCAAATTGTTCTCACCCAGTCTCC-3' along with (SEQ ID NO:2) 5'-TGGGCCCTTGGTGGAGGCTGAGGAGACTGTGAGAGTGGTGC-3' and (SEQ ID NO:4) 5'-GACAGATGGTGCAGCCACAGCCCGG TTTATTTCCAACTTTGTCC-3' for the respective variable regions.

For the human heavy and light chain constant region genes, a human leukocyte 5'-stretch plus cDNA library was purchased from Clontech (HL 5019t). Two PCR reactions were performed on this library using primers specific for the heavy and light chain constant regions, respectively (Heavy chain: (SEQ ID NO:6) 5'-GCACCACTCTCACAGTCTCCTCAGCCTCCACCAAGGGCCCA-3 and (SEQ ID NO:5) 5'-ATAAGAATGCGGCCGCTCATTTACCCGGAGACAGGGAG-3' for full length along with (SEQ ID NO:7) 5'-TGCGGCCGCTCATGGGCACGGTGGGCATGTGT-3'for FAB generation'; Light chain: (SEQ ID NO:9) 5'-GGACAAAGTTGGAAATAAACCGGGCTGTGGCTGCACCATCTGTC-3' and (SEQ ID NO:8) 5'-ATAAGAATGCGGCCGCTAACACTCTCCCTGTTGAAGCT-3'.

A DNA sequence encoding the mouse light chain variable region was fused in frame to a sequence encoding the human light chain constant region (SEQ ID NO: 11 and SEQ ID NO:12). A fragment encoding the final fusion construct was inserted into *P. pastoris* expression vector pGAPZ-alpha via ligation through 5'-XhoI and 3'-NotI sites in pGAPZ-alpha. DNA sequence encoding the mouse heavy variable region was fused in frame to sequences encoding each of the three human heavy chain constant regions. These fusion products were then inserted using a similar 5'-XhoI and 3'-NotI strategy into pGAPZ-alpha. (SEQ ID NO:13 and SEQ ID NO: 14 for the glycosylated version; SEQ ID NO: 15 for the aglycosylated version; SEQ ID NO: 16 for the Fab fragment). The proper antibody gene DNA sequences in all vectors were confirmed by direct DNA sequencing prior to further work.

Transformation of expression vectors into haploid ade1 ura3, met1 and lys3 host strains of *P. pastoris*. All methods used for transformation of haploid *P. pastoris* strains and genetic manipulation of the *P. pastoris* sexual cycle were as described in Higgins, D. R., and Cregg, J. M., Eds. 1998. *P. pastoris Protocols. Methods in Molecular Biology*. Humana Press, Totowa, N.J.

Prior to transformation, each expression vector was linearized within the GAP promoter sequences with AvrII to direct the integration of the vectors into the GAP promoter locus of the *P. pastoris* genome. Samples of each vector were then individually transformed into electrocompetent cultures of the ade1, ura3, met1 and lys3 strains by electroporation and successful transformants were selected on YPD Zeocin plates by their resistance to this antibiotic. Resulting colonies were selected, streaked for single colonies on YPD Zeocin plates and then examined for the presence of the antibody gene insert by a PCR assay on genomic DNA extracted from each strain for the proper antibody gene insert and/or by the ability of each strain to synthesize an antibody chain by a colony lift/immunoblot method (Wung et. al. Biotechniques 21 808-812 (1996). Haploid ade1, met1 and lys3 strains expressing one of the three heavy chain constructs were collected for diploid constructions along with haploid ura3 strain expressing light chain gene. The haploid strains expressing each of the heavy chain genes were mated with the appropriate light chain haploid ura3 strain to generate diploid secreting protein.

Mating of haploid strains synthesizing a single antibody chain and selection of diploid derivatives synthesizing tetrameric functional antibodies. To mate *P. pastoris* haploid strains, each ade1 (or met1 or lys3) heavy chain producing strain to be crossed was streaked across a rich YPD plate and the ura3 light chain producing strain was streaked across a second YPD plate (~10 streaks per plate). After one or two days incubation at 30° C., cells from one plate containing heavy chain strains and one plate containing ura3 light chain strains were transferred to a sterile velvet cloth on a replica-plating block in a cross hatched pattern so that each heavy chain strain contained a patch of cells mixed with each light chain strain. The cross-streaked replica plated cells were then transferred to a mating plate and incubated at 25° C. to stimulate the initiation of mating between strains. After two days, the cells on the mating plates were transferred again to a sterile velvet on a replica-plating block and then transferred to minimal medium plates. These plates were incubated at 30° C. for three days to allow for the selective growth of colonies of prototrophic diploid strains. Colonies that arose were picked and streaked onto a second minimal medium plate to single colony isolate and purify each diploid strain. The resulting diploid cell lines were then examined for antibody production.

Putative diploid strains were tested to demonstrate that they were diploid and contained both expression vectors for antibody production. For diploidy, samples of a strain were spread on mating plates to stimulate them to go through meiosis and form spores. Haploid spore products were collected and tested for phenotype. If a significant percentage of the resulting spore products were single or double auxotrophs we concluded that the original strain must have been diploid. Diploid strains were examined for the presence of both antibody genes by extracting genomic DNA from each and utilizing this DNA in PCR reactions specific for each gene.

Fusion of haploid strains synthesizing a single antibody chain and selection of diploid derivatives synthesizing tetrameric functional antibodies. As an alternative to the mating procedure described above, individual cultures of single-chain antibody producing haploid ade1 and ura3 strains were spheroplasted and their resulting spheroplasts fused using polyethylene glycol/CaCl$_2$. The fused haploid strains were then embedded in agar containing 1 M sorbitol and minimal medium to allow diploid strains to regenerate their cell wall and grow into visible colonies. Resulting colonies were picked from the agar, streaked onto a minimal medium plate, and the plates incubated for two days at 30° C. to generate colonies from single cells of diploid cell lines. The resulting putative diploid cell lines were then examined for diploidy and antibody production as described above.

Figure 2:
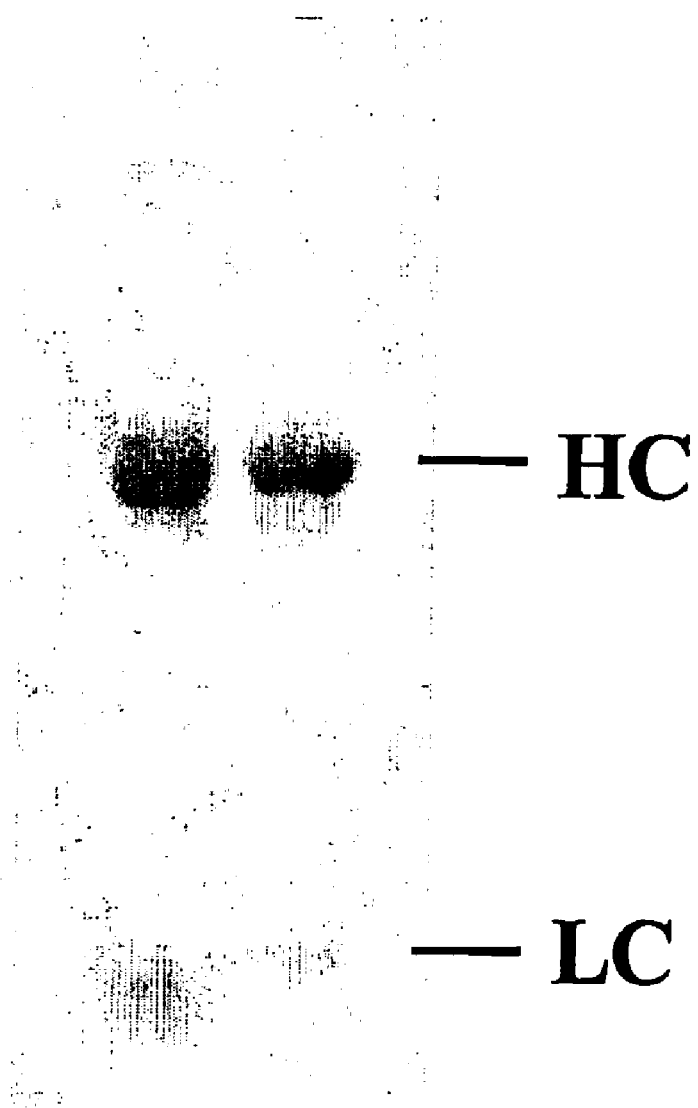
FIG. 2. Full length antibody production in *P. pastoris*. Heterologous expression of full-length antibody was conducted using a diploid *P. pastoris* strain. Exported antibody protein was isolated from conditioned medium using Protein A affinity chromatography. An aliquot of the peak fraction is shown. The human IgG standard was derived from purified pooled human IgG.

Purification and analysis of antibodies. A diploid strain for the production of full length antibody was derived through the mating of ura3 light chain strain 2252 and lys3 heavy chain strain 2254 using the methods described above. Culture media from shake-flask or fermenter cultures of diploid *P. pastoris* expression strains were collected and examined for the presence of antibody protein via SDS-PAGE and immunoblotting using antibodies directed against heavy and light chains of human IgG, or specifically against the heavy chain of IgG. The data is shown in FIG. 2.

Figure 3:
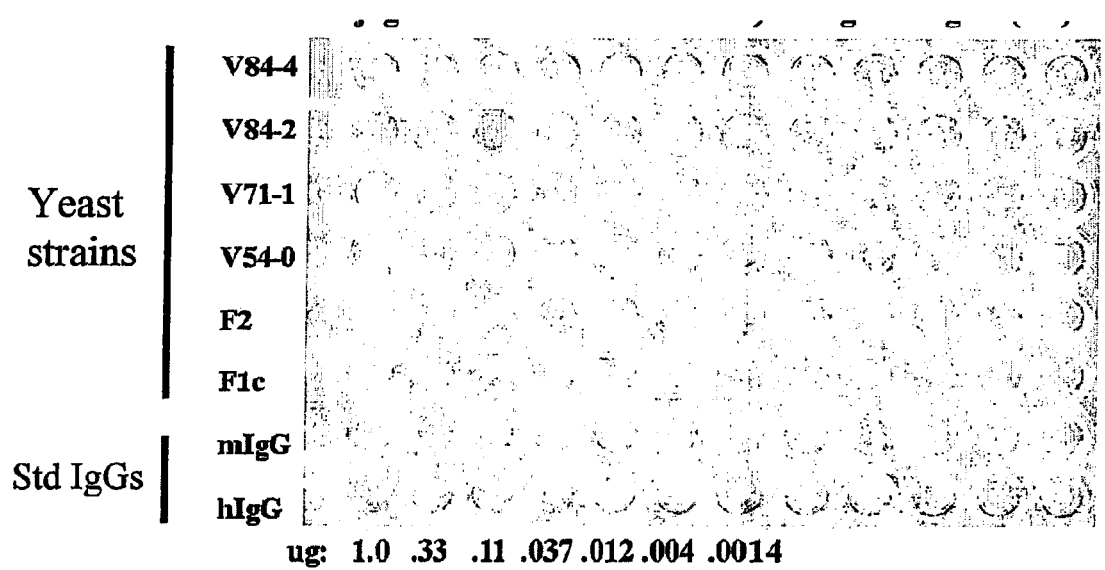
FIG. 3. Assembled antibody was detected and characterized from media supernatants from subclones of diploid *P. pastoris* strains, which were engineered to produce full-length mouse/human chimeric antibody. Microtiter plates were coated with Anti-human Fc selective antibodies to capture the antibody from the culture media. Correctly assembled antibody was detected through the use of a human selective (Fab')2, which recognized the paired heavy CH1 and κ light chain constant regions. Serial dilutions of clarified medium were applied to the plate. Development was through standard ELISA visualization methods. The detection is selective as shown by the lack of any detectable signal in the mIgG standard.

To purify the yeast secreted antibodies, clarified media from antibody producing cultures were passed through a protein A column and after washing with 20 mM sodium phosphate, pH 7.0, binding buffer, protein A bound protein was eluted using 0.1 M glycine HCl buffer, pH 3.0. Fractions containing the most total protein were examined by Coomasie blue strained SDS-PAGE and immunoblotting for antibody protein. Fractions were also examined via an ELISA assay in which microtiter plates were first coated with F(ab')2 goat anti-human IgG, Fcγ (Jackson Immuno, Cat No. 109-006-008). Next plates were reacted with selected dilutions of yeast made antibodies. Finally, plates were reacted with HRP-conjugated goat anti-human F(ab')2 fragment of IgG F(ab')2 (Jackson Immuno, Cat No. 109-036-097). Plates were then developed with TMP substrate (Sigma Chemical) and reactions were quenched with 0.5 M HCl. Results were quantitated on a BioRad microtiter plate reader at 415 nm. The data are illustrated in FIG. 3.

Assay for antibody activity. The recombinant yeast-derived chimeric antibody was evaluated for functional activity through immunohistochemical staining of cells containing the target antigen. The chimeric antibody selectively recognizes the CD3 complex found on T cells. Jurkat T cells were employed as a source of antigen and cell surface staining was conducted using procedures described in Andersson and Sander (Immunol Lett. 1989 Jan. 31; 20(2):115-20) or Andersson et. al. (Eur J. Immunol. 1988 December; 18(12):2081-4).

Figure 4:
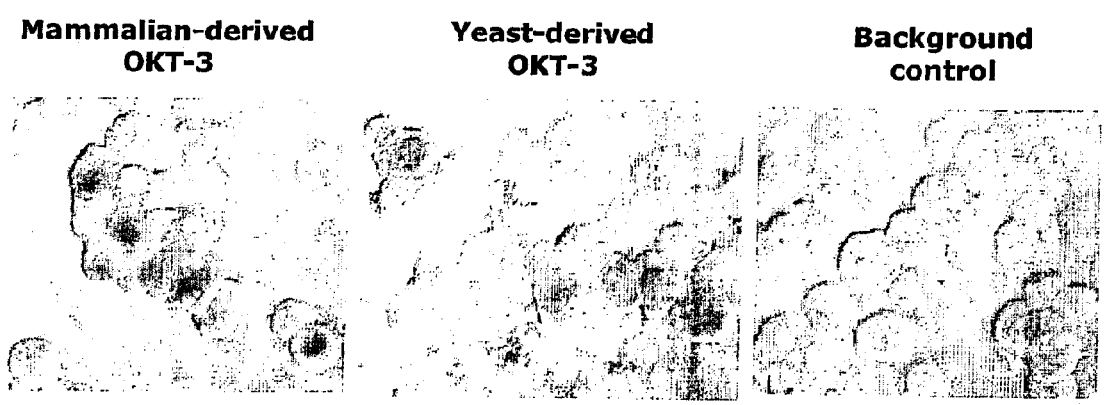
FIG. 4. *P. pastoris* generated recombinant antibody stains CD3 containing Jurkat T-cells as well as traditional mammalian-derived antibody. Jurkat T-cells were immobilized on glass slides and staining was conducted using the anti-CD3 antibody generated in yeast and mammalian cells. Detection was performed using a biotinylated-conjugated anti-rodent secondary antibody, and developed with an HRP-streptavidin derivative. The images are representative field of a slide treated with each recombinant antibody. Background is control for development and conducted in the absence of the primary anti-CD3 antibody.

Jurkat T cells were immobilized on glass slides, blocked with the appropriate blocking serum and stained with mammalian and yeast generated recombinant primary antibody for 1 hour. The immobilized samples were then treated with peroxidase blocking agent followed by staining with a biotinylated Fc selective secondary antibody that is specific for each form of the antibody (anti-mouse for the mammalian and anti-human for the yeast). Detection was performed using a HRP-Streptavidin system. Digital imaging was performed to collect the data for each stained sample. Positive signal is detected in samples via a dark staining of the cells observed in the panels for mammalian-derived and yeast-derived OKT-3. This is data is shown in FIG. 4.

Example 2

Identification of Novel P. pastoris Promoters

Objective:
P. pastoris has been developed into a robust scalable platform for industrial scale production of heterologous proteins for commercial applications. As noted previously, there is a need to expand the gene expression technology in this yeast strain for specific expression induction control of heterologous protein production in P. pastoris. Current inducible promoter systems employ materials that pose significant hazards at the scale-up stage. These studies were designed to investigate alternate regulated promoters in P. pastoris employing inexpensive, non-hazardous induction alternatives. Experimental data has now identified a series of novel promoters that operate using induction agents that fit this criterion.
Concept:
It is known from published data that some S. cerevisiae genes whose products are involved in central carbohydrate metabolism exhibit high expression levels under particular growing conditions and repressed under others. For example, many enzymes involved in gluconeogenesis are reduced in presence of glucose and dramatically increased when glucose is replaced by alternative carbon sources. This repression/activation is regulated at the transcriptional level and is controlled by the specificity of their promoters. Based on this conjecture, we have selected a number of P. pastoris genes that we expect may exhibit strong regulation (see Table 1).

TABLE 1

| Gene Selection | | |
| --- | --- | --- |
| P. pastoris gene | Enzyme Encoded | Level of induction in S. cerevisiae |
| PP-ACS1A | Acetyl-CoA synthetase | X 13 |
| PP-ACS1B | Acetyl-CoA synthetase | X 3 |
| PP-FPB1 | Fructose-1,6-phosphatase | X 14.4 |
| PP-ADH1 | Alcohol dehydrogenase | |
| PP-ADH2 | Alcohol dehydrogenase | |
| PP-PCK1A | Phosphoenolpyruvate carboxykinase | X 14.7 |
| PP-PCK1B | Phosphoenolpyruvate carboxykinase | X 14.7 |
| PP-PYC1A | Phosphoenolpyruvate carboxykinase | X 14.7 |
| PP-HXK1 | Hexokinase | X 5.8 |

TABLE 1-continued

| Gene Selection | | |
| --- | --- | --- |
| P. pastoris gene | Enzyme Encoded | Level of induction in S. cerevisiae |
| PP-PGI1 | Glucose-6-phosphate isomerase | |
| PP-PYC1 | Pyruvate carboxylase | X 3.1 |
| PP-GUT1 | Glycerol kinase | |
| PP-GUT2 | Glycerol-3-phosphate dehydrogenase | |
| PP-ALD2 | Aldehyde dehydrogenase | X 12.4 |
| PP-ALD6 (ALD2C) | Aldehyde dehydrogenase | X 12.4 |
| PP-PGM2 | Phosphoglucomutase | X 9.1 |
| PP-GSH2 | Glutathione synthetase | constitutive |
| PP-ENO1 | Enolase | X 3 |
| PP-PDC6 | Pyruvate decarboxylase | X 12 |

A second potential approach in identifying a strongly expressing and regulated promoter in P. pastoris is based on comparison of expression levels of cellular proteins in the wild type P. pastoris growing on selected carbon sources. Cell free extracts were obtained from the mid-logarithmic phase cells grown in liquid media with methanol, ethanol, glycerol or glucose. The proteins from each sample were separated by PAGE, transferred to a membrane, visualized by Coommassie blue staining and major protein bands that presumably represented proteins synthesized by higher expressing genes were analyzed by N-terminal sequencing. The resulting sequences were then analyzed. One notable result was the presence of a 46.5 kDa protein that is highly expressed in all but methanol medium which was identified as Eno1p (Enolase). A second 37 kDa protein representing a major protein induced by methanol was identified as NAD-dependent Formate Dehydrogenase (Fdh1p), and lastly a 58 kDa protein expressed at high levels in medium with ethanol was identified as Myo-Inositol-1-Phosphate Synthase (Ino1p).

These two strategies provided the genes that were used to interrogate the genomic sequence of P. pastoris to locate the appropriate promoter regions. From this bioinformatics strategy, molecular biology reagents were generated to recover upstream potential regulatory regions of these genes through a PCR-based approach.

Cloning of Promoters and Construction of Test Plasmids with b-lactamase Reporter Gene Five genes were chosen for further studies based on Table 1: GSH2, ENO1, PDC6, GUT1 and ADH1. As a reporter gene, a modified E. Coli®-lactamase gene with Zeo gene as selective marker in the vector backbone was chosen. This vector pPIC-bla can be easily modified through the insertion of a fragment using the 5' BglII and 3'BstBI cloning sites to drive β-lactamase expression. To introduce chosen DNA fragments into the vector, 5' primers containing sequences either for BamHI or BglII and 3' primers with NarI, BstBI or ClaI were designed. Each primer contained about 20 bp of sequence complementary to sequences 5' of the ORF of each gene. Typically constructs contain approximately 1000 bp of sequence upstream of the ORF. Using this strategy, P. pastoris genomic DNA was used as template and all five promoters were amplified by PCR followed by cloning into a TOPO vector. After sequencing to confirm that the correct sequences of the cloned fragments and presence of the cloning sites, the promoter test fragments were subcloned into BglII and BstBI-digested vector pPIC-bla. The correct structures of plasmids designated as pGSH2-blaZ, pENO1-blaZ, pPDC6-blaZ, pGUT1-blaZ and pADH1-blaZ were confirmed by PCR and DNA sequencing. All plasmids were linearized by digestion within a unique site located in the cloned fragments (promoters) and introduced by electroporation into wild type P. pastoris strain Y-11430. Zeocin resistant colonies were selected and analyzed by PCR for the presence of the hybrid (promoter-reporter gene) DNA. Positive transformants were also analyzed for expression of β-lactamase. As positive controls, transformants with pPICZ-bla (=pAOX1-blaZ: high expression of β-lactamase in methanol) and pGAP-blaZ (high constitutive expression of -lactamase) were used. As a negative control, a transformant of pPICZ-HSA expressing another protein under control of the AOX1 promoter was used.

Representative Example of Promoter Cloning

Waterham et al. (Gene 186, 1997) created the plasmid pHWO19A encoding an N-terminally truncated b-lac protein (gene designation: bla). The amino acid sequence of the modified bla gene has a 23 amino acid deletion and encodes amino acids from $His_{24}$ through $Trp_{286}$ (Sutcliffe, 1978) preceded by Met-Ser-Gly. This modified bla gene was introduced into pPICZ to obtain the bla gene under control of the AOX1 promoter.

The nucleotide sequence of the *P. pastoris* ADH1 promoter was amplified by PCR using *P. pastoris* genomic DNA as template and two primers 5IT221 and 3IT222:

```
5IT221:
                                    (SEQ ID NO: 29)
5'-GGATCCTTTTTACCACCCAAGTGC-3'

3IT222:
                                    (SEQ ID NO: 17)
5-ATCGATAAAAGCTAGTAGCTGATGGAAGAA-3'
```

The resulting 1033 bp PCR product was digested with BamHI and ClaI and ligated into vector pPICZ-bla digested with BglII and BstBI to replace the AOX1 promoter.

The nucleotide sequence of the *P. pastoris* ADH1 gene (SEQ ID NO:18) (promoter region intervenes the asterisked regions of the gene sequence, the remaining residues are the putative ORF):

```
                                    (SEQ ID NO: 18)
***TCCTTTTTACCACCCAAGTGCGAGTGAAACACCCCATGGCTGCTCTC

CGATTGCCCCTCTACAGGCATAAGGGTGTGACTTTGTGGGCTTGAATTTT

ACACCCCCTCCAACTTTTCTCGCATCAATTGATCCTGTTACCAATATTGC

ATGCCCGGAGGAGACTTGCCCCCTAATTTCGCGGCGTCGTCCCGGATCGC

AGGGTGAGACTGTAGAGACCCCACATAGTGACAATGATTATGTAAGAAGA

GGGGGGTGATTCGGCCGGCTATCGAACTCTAACAACTAGGGGGGTGAACA

ATGCCCAGCAGTCCTCCCCACTCTTTGACAAATCAGTATCACCGATTAAC

ACCCCAAATCTTATTCTCAACGGTCCCTCATCCTTGCACCCCTCTTTGGA

CAAATGGCAGTTAGCATTGGTGCACTGACTGACTGCCCAACCTTAAACCC

AAATTTCTTAGAAGGGGCCCATCTAGTTAGCGAGGGGTGAAAAATTCCTC

CATCGGAGATGTATTGACCGTAAGTTGCTGCTTAAAAAAATCAGTTCAG

ATAGCGAGACTTTTTTGATTTCGCAACGGGAGTGCCTGTTCCATTCGATT

GCAATTCTCACCCCTTCTGCCCAGTCCTGCCAATTGCCCATGAATCTGCT

AATTTCGTTGATTCCCACCCCCCTTTCCAACTCCACAAATTGTCCAATCT

CGTTTTCCATTTGGGAGAATCTGCATGTCGACTACATAAAGCGACCGGTG

TCCGAAAAGATCTGTGTAGTTTTCAACATTTTGTGCTCCCCCCGCTGTTT

GAAAACGGGGGTGAGCGCTCTCCGGGGTGCGAATTCGTGCCCAATTCCTT

TCACCCTGCCTATTGTAGACGTCAACCCGCATCTGGTGCGAATATAGCGC

ACCCCCAATGATCACACCAACAATTGGTCCACCCCTCCCCAATCTCTAAT
```

-continued
```
ATTCACAATTCACCTCACTATAAATACCCCTGTCCTGCTCCCAAATTCTT

TTTTCCTTCTTCCATCAGCTACTAGCTTTTATCTTATTTACTTTACGAAA

***ATGTCTCCAACTATCCCAACTACACAAAAGGCTGTTATCTTCGAGAC

CAACGGCGGTCCCCTAGAGTACAAGGACATTCCAGTCCCAAAGCCAAAGT

CAAACGAACTTTTGATCAACGTTAAGTACTCCGGTGTCTGTCACACTGAT

TTGCACGCCTGGAAGGGTGACTGGCCATTGGACAACAAGCTTCCTTTGGT

TGGTGGTCACGAAGGTGCTGGTGTCGTTGTCGCTTACGGTGAGAACGTCA

CTGGATGGGAGATCGGTGACTACGCTGGTATCAAATGGTTGAACGGTTCT

TGTTTGAACTGTGAGTACTGTATCCAAGGTGCTGAATCCAGTTGTGCCAA

GGCTGACCTGTCTGGTTTCACCCACGACGGATCTTTCCAGCAGTATGCTA

CTGCTGATGCCACCCAAGCCGCCAGAATTCCAAAGGAGGCTGACTTGGCT

GAAGTTGCCCCAATTCTGTGTGCTGGTATCACCGTTTACAAGGCTCTTAA

GACCGCTGACTTGCGTATTGGCCAATGGGTTGCCATTTCTGGTGCTGGTG

GAGGACTGGGTTCTCTTGCCGTTCAATACGCCAAGGCTCTGGGTTTGAGA

GTTTTGGGTATTGATGGTGGTGCCGACAAGGTGAATTTGTCAAGTCCTTG

GGTGCTGAGGTCTTCGTCGACTTCACTAAGACTAAGGACGTCGTTGCTGA

AGTCCAAAAGCTCACCAACGGTGGTCCACACGGTGTTATTAACGTCTCCG

TTTCCCCACATGCTATCAACCAATCTGTCCAATACGTTAGAACTTTGGGT

AAGGTTGTTTTGGTTGGTCTGCCATCTGGTGCCGTTGTCAACTCTGACGT

TTTCTGGCACGTTCTGAAGTCCATCGAGATCAAGGGATCTTACGTTGGAA

ACAGAGAGGACAGTGCCGAGGCCATCGACTTGTTCACCAGAGGTTTGGTC

AAGGCTCCTATCAAGATTATCGGTCTGTCTGAACTTGCTAAGGTCTACGA

ACAGATGGAGGCTGGTGCCATCATCGGTAGATACGTTGTGGACACTTCCA

AATAA
```

The putative amino acid sequence of the *P. pastoris* ADH1 protein is:

```
                                    (SEQ ID NO: 19)
MSPTIPTTQKAVIFETNGGPLEYKDIPVPKPKSNELLINVKYSGVCHTDL

HAWKGDWPLDNKLPLVGGHEGAGVVVAYGENVTGWEIGDYAGIKWLNGSC

LNCEYCIQGAESSCAKADLSGFTHDGSFQQYATADATQAARIPKEADLAE

VAPILCAGITVYKALKTADLRIGQWVAISGAGGGLGSLAVQYAKALGLRV

LGIDGGADKGEFVKSLGAEVFVDFTKTKDVVAEVQKLTNGGPHGVINVSV

SPHAINQSVQYYRTLGKVVLVGLPSGAVVNSDVFWHVLKSIEIKGSYVGN

REDSAEAIDLFTRGLVKAPIKIIGLSELAKVYEQMEAGAIIGRYVVDTSK
```

The subsequent promoter constructs were generated in a similar fashion using the sequences demarked below specific to each promoter fragment. Note: Primers used to amplify from the 5' and 3' ends of the genomic sequence are found at the start of each section.

ENO1:
5IT215:
```
                                    (SEQ ID NO: 20)
5'-AGATCTGGGCAAAATCACACAATTC-3'
```

```
3IT216:
                                                  (SEQ ID NO: 21)
5'-TTCGAATTGTTATAATTGTGTGTTTCAACCAAG-3'

(SEQ ID NO: 22)
AGATCTGGGCAAAATCACACAATTCCAAACCATGCTAAATGAGATTTAAA

GAACAAACGATGGCAAAAGGCAACCGTTATAAATGTGATCTTTCTTGGCA

GTTATCTGTCAATTTTTCTAAGGAACAGTGAATTCATCATAGGAGAGATG

TTATACGTTACATAATCATACATACTGCATGTATCTCACCTACTTTACCT

CATCAACTCTAAAACAGTTCTAGTCCCAACCCCAGATTCCTAGTCATGAC

ACAAGTCCGCACCGGACAGGACTCACAACCAGCAAGAGAAGCTAACAAAT

TTACGCCCCGGTAAAACATTCCTTAGGGGCCGTTCAATGGTAATTTTCCT

CTCACCCGTTTAAACTTACCTCCGGGCGGTATCTTCAATAACCTCTGTTG

TCCCCGGGTATCATTGGAAACAGTGAGGGACGTTGAACAGAAGAGAGGAT

CACCGTAAATTTGCCTTGCAATTGGCCCTAACCACGGATGGTTAACTTCA

AGCCATCACGACAGCAATTGAGTCGGCGCATAGCTACCCTCCTCTTCTTG

ACCCCATGCATAGGACCAACCTTAACCGATGGAACAGGTTCCTCCGCTCC

GTCCCCTGGTAGTGTCTCTGCGCAAGAAATAGTTAAGGTATGAAGACTGA

TCTCTCGCACCCCCCTCACAGTACTGTTATGGTGAATTGACAAAGCCATT

GGCTAGATTGAAACATGTAATTCATATGTAATCTTGTTCAATTAACGAGC

TTCGTACAGTCTCAATCTAGACGTCTGATAATGGCGTTTGTGCTCCTAAT

CGATGAGCCATCTCATGTGACGTCTATACGCTTCGATGGCTTCCGTCGCG

AATATAGAACCACTTGAAATATGCTGCAAACCACGATCCACCCTGGTCCT

GAAAAGATATAAATACAGCACATCTAGCAGGCTTTTGTCTTCTTGGTTGA

AACACACAATTATAACAATTCGAA

PDC6:
5IT217:
                                                  (SEQ ID NO: 23)
5'-AGATCTAAAGCATTGCTGAGCAATATTTC-3'

3IT218:
                                                  (SEQ ID NO: 24)
5'-ATCGATGTACTAGCTAATTGATTGATGATTAACG-3'

(SEQ ID NO: 25)
AGATCTAAAGCATTGCTGAGCAATATTTCGGATCAACATCAACAGAATAG

ATCGTCACCACGAAGTATATCCAACTATTCCCCAAGAATCCAGGCTTATC

CCTCAAGAATGGCCTCTCCATCTCCTTCAATGAAGATGGCATTGACAAAC

TCCGTCAGCTTGCAGGATACAATGGATGCGGAACTAGAAGCGTTGGCAAA

CGAACAATATTACGTCATGCTAGATATCCTTAAGGGATTTTGCGATCTTT

CATTTGACATGGTAAACATATTTTCTATCCAGATCCCTGAGGTATTACAT

CTCCTCTTCGGCTTTGGTGCAGGGTCACTGGCCTTAACGGGAGTCGTATC

CAAAACGAGACAAGAACTAATAAATAAACAGATATAAGGGACAAGCACAC

GATTACCCAATCACTTGATATGCACCAATTTGTTCCGTTGTTTATGCCAT

ATTTACCGAATTTTCTTCCCAGGTTTTTCCGAATGGACATCTGTAGTCCA

CTTTTTGGTTATCATAATCGTCCCACAAGTCGTGGATTTAACCAGAACCT

AGTAATTTTAAGTTCGCTATTAATCACTCAGAATGGTCTCACCTTGCTAT

TGGCCAAGTCTGGAGTCGCCAGCTACCACCTCAGAGGCTACATAGACCTC

CCAATGTCATCTCCTCAGTGCGCTCTTCAATCTCGTGTCTTTTCCGTTAA

AACTCCGTTCGTTTCACCCTATACTGCCCCTGGTTGTGCAGCTCTTACCA

CTTCGCGCCGCTACTATCCGTAGTGGTCGAGCCGCATCAATATCACGTTG

AAATAGAATAACTCCCTACAAAAGCCGCACGCAACCATCAAATCTATATA

AGGAACCTCAAATATCTAGCAACATCTTTTCAATTTACTACAACATATTC

GTTAATCATCAATCAATTAGCTAGTACATCGAT

GUT1:
5IT219:
                                                  (SEQ ID NO: 26)
5'-AGATCTTTCAAGTCGGACCCCAACT-3'

3IT220:
                                                  (SEQ ID NO: 27)
5'-GGCGCCTGTGGTATAGTGTGAAAAAGTAGAAGAAG-3'

(SEQ ID NO: 28)
TTTCAAGTCGGACCCCAACTTTCAAGTGACCCAATTTAGCAGCCTGCATT

CTCTTGATTTTATGGGGGAAACTAACAATAGTGTTGCCTTGATTTTAAGT

GGCATTGTTCTTTGAAATCGAAATTGGGGATAACGTCATACCGAAAGGTA

AACAACTTCGGGGAATTGCCCTGGTTAAACATTTATTAAGCGAGATAAAT

AGGGGATAGCGAGATAGGGGCGGAGAAGAAGAAGGGTGTTAAATTGCTG

AAATCTCTCAATCTGGAAGAAACGGAATAAATTAACTCCTTCCTGAGATA

ATAAGATCCGACTCTGCTATGACCCCACACGGTACTGACCTCGGCATACC

CCATTGGATCTGGTGCGAAGCAACAGGTCCTGAAACCTTTATCACGTGTA

GTAGATTGACCTTCCAGCAAAAAAAGGCATTATATATTTTGTTGTTGAAG

GGGTGAGGGGAGGTGCAGGTGGTTCTTTTATTCGTCTTGTAGTTAATTTT

CCCGGGGTTGCGGAGCGTCAAAAGTTTGCCCGATCTGATAGCTTGCAAGA

TGCCACCGCTTATCCAACGCACTTCAGAGAGCTTGCCGTAGAAAGAACGT

TTTCCTCGTAGTATTCCAGCACTTCATGGTGAAGTCGCTATTTCACCGAA

GGGGGGGTATTAAGGTTGCGCACCCCCTCCCCACACCCCAGAATCGTTTA

TTGGCTGGGTTCAATGGCGTTTGAGTTAGCACATTTTTTCCTTAAACACC

CTCCAAACACGGATAAAAATGCATGTGCATCCTGAAACTGGTAGAGATGC

GTACTCCGTGCTCCGATAATAACAGTGGTGTTGGGGTTGCTGTTAGCTCA

CGCACTCCGTTTTTTTTTCAACCAGCAAAATTCGATGGGGAGAAACTTGG

GGTACTTTGCCGACTCCTCCACCATACTGGTATATAAATAATACTCGCCC

ACTTTTCGTTTGCTGCTTTTATATTTCAAGGACTGAAAAAGACTCTTCTT

CTACTTTTTCACACTATACCACAGGCGCC
```

Promoter Induction Studies

The promoter containing strains were evaluated under a series of conditions to test the selectivity of different glycolytic agents and the influence these agents have towards the induction of the reporter gene. β-lactamase levels are directly proportional to the strength of induction by the test agent. A subset of table 1 was explored in these studies.

P. pastoris transformants containing the constructions were grown in 50 ml buffered (pH6.0) liquid YNB medium with methanol, ethanol, glycerol or glucose for 28 h and samples were collected every 5 h. Cell-free extracts of each cell sample were prepared and analyzed for protein concentration using Pierce BCA reagent and for β-lactamase activity using PADAC as substrate. The normalization of protein enables assessment of the efficiency of the induction. The results of this analysis are summarized in Table 2.

TABLE 2

Comparison of b-lactamase specific activities in *P. pastoris*

| Expression cassette: | b-lactamase activity compared to activity of pGAP1-bla on glucose at 20 h (no - no activity, ww - very weak, w—weak, h—high Carbon source | | | | Properties of the promoter |
|---|---|---|---|---|---|
| | Glucose | Glycerol | Ethanol | Methanol | |
| pGSH2-bla | w | w | w | w | Weak constitutive |
| pADH1-bla | w | h | h | ww | Strong, induced by glycerol and ethanol |
| pGUT1-bla | w | h | w | w | Strong, induced by glycerol |
| pENO1-bla | h | h | h | w | Strong, repressed by methanol |
| pPDC6-bla | h | h | h | w | Strong, repressed by methanol |
| pGAP1-bla | h | h | h | h | Strong constitutive, partially repressed by methanol and glycerol |
| pAOX1-bla | no | ww | no | h | Strong, induced by methanol |
| pAOX1-GSH | no | no | no | no | |

These experimental results highlight the following advantages of the invention:
1. *P. pastoris* ADH1 promoter induction profile is consistent with the yeast physiology in the two metabolic conditions shown to have strong enzyme induction and this inductions is significant with selective carbon sources.
2. The GUT1 promoter whose gene encodes glycerol kinase selectively response to glycerol, which is again consistent with the metabolic pathway, in which this gene operates.
3. The endolase gene (ENO1) promoter responds to broad carbon sources, which is in line with the central biochemistry this enzyme plays in carbon metabolism.

Conclusions and Applications of the Subject Novel Promoters

To date the dominant regulated promoters employed in the *P. pastoris* expression system are from the following genes: AOX1, FLD and GAP. The three promoters ADH1, GUT1 and ENO1 are novel and have not previously been characterized from *P. pastoris*. The AOX1 promoter system is the dominant inducible system in *P. pastoris* and suffers from the scale-up need of significant oxygen and methanol feeds in the fermenter. This is an extremely combustible combination and requires extensive control to ensure a non-hazardous process. In the case of the FLD promoter system, which has not seen wide implementation, the inducing agent is either methanol or a highly volatile toxic alkyl amine. The 3 new promoters offer pronounced advantages due to the nature of the induction agents used which are inexpensive as well as non-hazardous in nature. As such they possess characteristics important in commercialization process development. In addition, in the case of the ADH1 promoter there is significant induction by the promoter for the reporter under conditions where elevated ethanol is present either through rich carbon feeding (through the use of glycerol) or direct exposure to alcohol. There are clear feeding strategies during fermentation where this promoter system can be kept in a tight off state and then switching to a carbon support strategy that initiates bulk product generation under high cell density conditions. In certain instances depending on the heterologous protein being expressed there can be significant advantages for this level of control. These range from increased overall protein production, enhanced stability and the ability to successfully generate protein product under conditions in which the expressed protein is toxic.

All references and publications referenced herein are incorporated by reference in their entireties.

In order to better illustrate the invention and its applications the following claims are provided.

What is claimed is:

1. A nucleic acid construct containing an isolated nucleic acid sequence containing a *P. pastoris* alcohol dehydrogenase gene (ADH1) promoter having the nucleic acid sequence intervening nucleotides 1 to 1048 of SEQ ID NO: 18 operably linked to a structural gene which promoter directs the transcription of said structural gene under inducible conditions; wherein said inducible conditions comprise the expression of said structural gene operably linked to said promoter in the presence of ethanol or glycerol or a mixed feed comprising ethanol and glycerol.

2. The nucleic acid construct of claim 1 wherein the promoter is operably linked to a structural gene other than ADH1.

3. The nucleic acid construct of claim 1 which is contained on a plasmid.

4. The nucleic acid construct of claim 3 wherein said plasmid is an autonomously replicating plasmid or one which integrates into the chromosomal DNA of a yeast.

5. A yeast cell which contains a plasmid according to claim 3.

6. The yeast cell of claim 5 which is a *P. pastoris, Candida, Saccharomyces, Yarrowia, Kluyveromyces, Hansenula*, or *Schizosaccharomyces* yeast cell.

7. The yeast cell of claim 6 which is polyploid.

8. The yeast cell of claim 7 which is a *P. pastoris* yeast.

9. A method of using a yeast cell according to claim 5 to produce a desired protein under the regulatory control of said ADH1 promoter, comprising growing the yeast cell under inducible conditions to produce the desired protein.

10. The method of claim 9 wherein said protein is multichain.

11. The method of claim 9 wherein said protein is a mammalian protein.

12. The method of claim 11 wherein said protein is an antibody or fragment thereof.

13. The method of claim 12 wherein said antibody or fragment is specific to a cytokine, or growth factor.

14. The method of claim 13 wherein the cytokine is selected from interleukins, an interferon, a tumor necrosis factor or a colony stimulating factor and the growth factor is a VEGF.

15. The method of claim 9 wherein said yeast cell is cultured in the presence of an amount of glycerol or ethanol or a mixed feed containing a sufficient amount of glycerol or ethanol to induce expression.

16. The method of claim 15 wherein said yeast cell contains at least one auxotrophic mutation, which requires supplementation for growth.

17. The method of claim 14 wherein the cytokine is selected from IL-2, IL-4, IL-6, IL-12, IL-13, interferon alpha, beta, or gamma, tumor necrosis factor or a colony stimulating factor.

18. The yeast cell of claim 5 which is a *Pichia* yeast cell.

* * * * *

```
                       SEQUENCE LISTING

<160> NUMBER OF SEQ ID NOS: 29

<210> SEQ ID NO 1
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccgctcgaga aaagagaggc tgaagctcag gtccagctgc agcagtc                    47

<210> SEQ ID NO 2
<211> LENGTH: 41
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 2
tgggcccttg gtggaggctg aggagactgt gagagtggtg c                            41

<210> SEQ ID NO 3
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccgctcgaga aaagagaggc tgaagctcaa attgttctca cccagtctcc                   50

<210> SEQ ID NO 4
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gacagatggt gcagccacag cccggtttat ttccaacttt gtcc                         44

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ataagaatgc ggccgctcat ttacccggag acagggag                               38

<210> SEQ ID NO 6
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcaccactct cacagtctcc tcagcctcca ccaagggccc a                            41

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgcggccgct catgggcacg gtgggcatgt gt                                     32

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ataagaatgc ggccgctaac actctcccct gttgaagct                    39

<210> SEQ ID NO 9
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggacaaagtt ggaaataaac cgggctgtgg ctgcaccatc tgtc              44

<210> SEQ ID NO 10

<400> SEQUENCE: 10

000

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
atcgataaaa gctagtagct gatggaagaa                              30

<210> SEQ ID NO 18
<211> LENGTH: 2100
<212> TYPE: DNA
<213> ORGANISM: Pichia pastoris

<400> SEQUENCE: 18

```
tccttttttac cacccaagtg cgagtgaaac accccatggc tgctctccga ttgcccctct      60
acaggcataa gggtgtgact ttgtgggctt gaattttaca cccctccaa ctttctcgc        120
atcaattgat cctgttacca atattgcatg cccggaggag acttgcccc taatttcgcg       180
gcgtcgtccc ggatcgcagg gtgagactgt agagacccca catagtgaca atgattatgt     240
aagaagaggg gggtgattcg gccggctatc gaactctaac aactaggggg gtgaacaatg     300
cccagcagtc ctccccactc tttgacaaat cagtatcacc gattaacacc ccaaatctta     360
ttctcaacgg tccctcatcc ttgcacccct ctttggacaa atggcagtta gcattggtgc     420
actgactgac tgcccaacct aaacccaaa tttcttagaa ggggcccatc tagttagcga      480
ggggtgaaaa attcctccat cggagatgta ttgaccgtaa gttgctgctt aaaaaaaatc     540
agttcagata gcgagacttt tttgatttcg caacgggagt gcctgttcca ttcgattgca     600
attctcaccc cttctgccca gtcctgccaa ttgcccatga atctgctaat ttcgttgatt     660
cccaccccc tttccaactc cacaaattgt ccaatctcgt tttccatttg ggagaatctg      720
catgtcgact acataaagcg accggtgtcc gaaaagatct gtgtagtttt caacattttg     780
tgctcccccc gctgtttgaa acgggggtg agcgctctcc ggggtgcgaa ttcgtgccca      840
attcctttca ccctgcctat tgtagacgtc aacccgcatc tggtgcgaat atagcgcacc     900
cccaatgatc acaccaacaa ttggtccacc cctccccaat ctctaatatt cacaattcac     960
ctcactataa ataccctgt cctgctccca aattcttttt tccttcttcc atcagctact     1020
agcttttatc ttatttactt tacgaaaatg tctccaacta tcccaactac acaaaaggct     1080
gttatcttcg agaccaacgg cggtcccta gagtacaagg acattccagt cccaaagcca     1140
aagtcaaacg aacttttgat caacgttaag tactccggtg tctgtcacac tgatttgcac     1200
gcctggaagg gtgactggcc attggacaac aagcttcctt tggttggtgg tcacgaaggt     1260
gctggtgtcg ttgtcgctta cggtgagaac gtcactggat gggagatcgg tgactacgct     1320
ggtatcaaat ggttgaacgg ttcttgtttg aactgtgagt actgtatcca aggtgctgaa     1380
tccagttgtg ccaaggctga cctgtctggt tcacccacg acggatcttt ccagcagtat     1440
gctactgctg atgccaccca agccgccaga attccaaagg aggctgactt ggctgaagtt     1500
gccccaattc tgtgtgctgg tatcaccgtt tacaaggctc ttaagaccgc tgacttgcgt     1560
attggccaat gggttgccat ttctggtgct ggtggaggac tgggttctct tgccgttcaa     1620
tacgccaagg ctctgggttt gagagttttg ggtattgatg tggtgccga caagggtgaa     1680
tttgtcaagt ccttgggtgc tgaggtcttc gtcgacttca ctaagactaa ggacgtcgtt     1740
gctgaagtcc aaaagctcac caacggtggt ccacacggtg ttattaacgt ctccgtttcc     1800
ccacatgcta tcaaccaatc tgtccaatac gttagaactt gggtaaggt tgttttggtt     1860
ggtctgccat ctggtgccgt tgtcaactct gacgttttct ggcacgttct gaagtccatc     1920
gagatcaagg gatcttacgt tggaaacaga gaggacagtg ccgaggccat cgacttgttc     1980
accagaggtt tggtcaaggc tcctatcaag attatcggtc tgtctgaact tgctaaggtc     2040
tacgaacaga tggaggctgg tgccatcatc ggtagatacg ttgtggacac ttccaaataa     2100
```

<210> SEQ ID NO 19

<211> LENGTH: 350
<212> TYPE: PRT
<213> ORGANISM: Pichia pastoris

<400> SEQUENCE: 19

Met Ser Pro Thr Ile Pro Thr Thr Gln Lys Ala Val Ile Phe Glu Thr
1               5                   10                  15

Asn Gly Gly Pro Leu Glu Tyr Lys Asp Ile Pro Val Pro Lys Pro Lys
            20                  25                  30

Ser Asn Glu Leu Leu Ile Asn Val Lys Tyr Ser Gly Val Cys His Thr
        35                  40                  45

Asp Leu His Ala Trp Lys Gly Asp Trp Pro Leu Asp Asn Lys Leu Pro
    50                  55                  60

Leu Val Gly Gly His Glu Gly Ala Gly Val Val Ala Tyr Gly Glu
65                  70                  75                  80

Asn Val Thr Gly Trp Glu Ile Gly Asp Tyr Ala Gly Ile Lys Trp Leu
                85                  90                  95

Asn Gly Ser Cys Leu Asn Cys Glu Tyr Cys Ile Gln Gly Ala Glu Ser
            100                 105                 110

Ser Cys Ala Lys Ala Asp Leu Ser Gly Phe Thr His Asp Gly Ser Phe
        115                 120                 125

Gln Gln Tyr Ala Thr Ala Asp Ala Thr Gln Ala Ala Arg Ile Pro Lys
    130                 135                 140

Glu Ala Asp Leu Ala Glu Val Ala Pro Ile Leu Cys Ala Gly Ile Thr
145                 150                 155                 160

Val Tyr Lys Ala Leu Lys Thr Ala Asp Leu Arg Ile Gly Gln Trp Val
                165                 170                 175

Ala Ile Ser Gly Ala Gly Gly Leu Gly Ser Leu Ala Val Gln Tyr
            180                 185                 190

Ala Lys Ala Leu Gly Leu Arg Val Leu Gly Ile Asp Gly Gly Ala Asp
    195                 200                 205

Lys Gly Glu Phe Val Lys Ser Leu Gly Ala Glu Val Phe Val Asp Phe
210                 215                 220

Thr Lys Thr Lys Asp Val Val Ala Glu Val Gln Lys Leu Thr Asn Gly
225                 230                 235                 240

Gly Pro His Gly Val Ile Asn Val Ser Val Ser Pro His Ala Ile Asn
                245                 250                 255

Gln Ser Val Gln Tyr Val Arg Thr Leu Gly Lys Val Val Leu Val Gly
            260                 265                 270

Leu Pro Ser Gly Ala Val Val Asn Ser Asp Val Phe Trp His Val Leu
        275                 280                 285

Lys Ser Ile Glu Ile Lys Gly Ser Tyr Val Gly Asn Arg Glu Asp Ser
    290                 295                 300

Ala Glu Ala Ile Asp Leu Phe Thr Arg Gly Leu Val Lys Ala Pro Ile
305                 310                 315                 320

Lys Ile Ile Gly Leu Ser Glu Leu Ala Lys Val Tyr Glu Gln Met Glu
                325                 330                 335

Ala Gly Ala Ile Ile Gly Arg Tyr Val Val Asp Thr Ser Lys
            340                 345                 350

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
agatctgggc aaaatcacac aattc                                                25

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ttcgaattgt tataattgtg tgtttcaacc aag                                        33

<210> SEQ ID NO 22
<211> LENGTH: 974
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 22
agatctgggc aaaatcacac aattccaaac catgctaaat gagatttaaa gaacaaacga            60
tggcaaaagg caaccgttat aaatgtgatc tttcttggca gttatctgtc aattttctta          120
aggaacagtg aattcatcat aggagagatg ttatacgtta cataatcata catactgcat          180
gtatctcacc tactttacct catcaactct aaaacagttc tagtcccaac cccagattcc          240
tagtcatgac acaagtccgc accggacagg actcacaacc agcaagagaa gctaacaaat          300
ttacgccccg gtaaaacatt ccttaggggc cgttcaatgg taattttcct ctcacccgtt          360
taaacttacc tccgggcggt atcttcaata acctctgttg tccccgggta tcattggaaa          420
cagtgaggga cgttgaacag aagagaggat caccgtaaat ttgccttgca attggcccta          480
accacggatg gttaacttca agccatcacg acagcaattg agtcggcgca tagctaccct          540
cctcttcttg accccatgca taggaccaac cttaaccgat ggaacaggtt cctccgctcc          600
gtcccctggt agtgtctctg cgcaagaaat agttaaggta tgaagactga tctctcgcac          660
ccccctcaca gtactgttat ggtgaattga caaagccatt ggctagattg aaacatgtaa          720
ttcatatgta atcttgttca attaacgagc ttcgtacagt ctcaatctag acgtctgata          780
atggcgtttg tgctcctaat cgatgagcca tctcatgtga cgtctatacg cttcgatggc          840
ttccgtcgcg aatatagaac cacttgaaat atgctgcaaa ccacgatcca ccctggtcct          900
gaaaagatat aaatacagca catctagcag gcttttgtct tcttggttga aacacacaat          960
tataacaatt cgaa                                                            974

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
agatctaaag cattgctgag caatatttc                                            29

<210> SEQ ID NO 24
<211> LENGTH: 34
<212> TYPE: DNA

<213> ORGANISM: Artificial Sequence
<220> FEATURE:
<223> OTHER INFORMATION: Description of Artificial Sequence: Synthetic primer

<400> SEQUENCE: 24
atcgatgtac tagctaattg attgatgatt aacg                               34

<210> SEQ ID NO 25
<211> LENGTH: 933
<212> TYPE: DNA
<213> ORGANISM: Artificial Sequence
<220> FEATURE:
<223> OTHER INFORMATION: Description of Artificial Sequence: Synthetic construct

<400> SEQUENCE: 25
agatctaaag cattgctgag caatatttcg gatcaacatc aacagaatag atcgtcacca    60
cgaagtatat ccaactattc cccaagaatc caggcttatc cctcaagaat ggcctctcca   120
tctccttcaa tgaagatggc attgacaaac tccgtcagct tgcaggatac aatggatgcg   180
gaactagaag cgttggcaaa cgaacaatat tacgtcatgc tagatatcct taagggattt   240
tgcgatcttt catttgacat ggtaaacata ttttctatcc agatccctga ggtattacat   300
ctcctcttcg gctttggtgc agggtcactg gccttaacgg gagtcgtatc caaaacgaga   360
caagaactaa taaataaaca gatataaggg acaagcacac gattacccaa tcacttgata   420
tgcaccaatt tgttccgttg tttatgccat atttaccgaa tttctttccc aggtttttcc   480
gaatggacat ctgtagtcca ctttttggtt atcataatcg tcccacaagt cgtggattta   540
accagaacct agtaatttta agttcgctat taatcactca gaatggtctc accttgctat   600
tggccaagtc tggagtcgcc agctaccacc tcagaggcta catagacctc ccaatgtcat   660
ctcctcagtg cgctcttcaa tctcgtgtct tttccgttaa aactccgttc gtttcaccct   720
atactgcccc tggttgtgca gctcttacca cttcgcgccg ctactatccg tagtggtcga   780
gccgcatcaa tatcacgttg aaatagaata actccctaca aaagccgcac gcaaccatca   840
aatctatata aggaacctca aatatctagc aacatctttt caatttacta caacatattc   900
gttaatcatc aatcaattag ctagtacatc gat                               933

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
agatctttca gtcggaccc caact                                          25

<210> SEQ ID NO 27
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
ggcgcctgtg gtatagtgtg aaaaagtaga agaag                              35

<210> SEQ ID NO 28

```
<211> LENGTH: 1029
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 28
tttcaagtcg  gaccccaact  ttcaagtgac  ccaatttagc  agcctgcatt  ctcttgattt     60 tatggggaa   actaacaata  gtgttgcctt  gattttaagt  ggcattgttc  tttgaaatcg    120
aaattgggga  taacgtcata  ccgaaaggta  aacaacttcg  gggaattgcc  ctggttaaac    180
atttattaag  cgagataaat  aggggatagc  gagatagggg  gcggagaaga  agaagggtgt    240
taaattgctg  aaatctctca  atctggaaga  aacggaataa  attaactcct  tcctgagata    300
ataagatccg  actctgctat  gaccccacac  ggtactgacc  tcggcatacc  ccattggatc    360
tggtgcgaag  caacaggtcc  tgaaaccttt  atcacgtgta  gtagattgac  cttccagcaa    420
aaaaaggcat  tatatatttt  gttgttgaag  gggtgagggg  aggtgcaggt  ggttcttta    480 ttcgtcttgt  agttaatttt  cccggggttg  cggagcgtca  aaagtttgcc  cgatctgata    540
gcttgcaaga  tgccaccgct  tatccaacgc  acttcagaga  gcttgccgta  gaaagaacgt    600
tttcctcgta  gtattccagc  acttcatggt  gaagtcgcta  tttcaccgaa  ggggggggtat   660 taaggttgcg  caccccctcc  ccacacccca  gaatcgttta  ttggctgggt  tcaatggcgt    720
ttgagttagc  acatttttc   cttaaacacc  ctccaaacac  ggataaaaat  gcatgtgcat    780
cctgaaactg  gtagagatgc  gtactccgtg  ctccgataat  aacagtggtg  ttggggttgc    840
tgttagctca  cgcactccgt  ttttttttca  accagcaaaa  ttcgatgggg  agaaacttgg    900
ggtactttgc  cgactcctcc  accatactgg  tatataaata  atactcgccc  acttttcgtt    960
tgctgctttt  atatttcaag  gactgaaaaa  gactcttctt  ctactttttc  acactatacc   1020
acaggcgcc                                                              1029

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ggatcctttt taccacccaa gtgc                                               24
```